(12) United States Patent
Germain et al.

(10) Patent No.: US 11,766,291 B2
(45) Date of Patent: Sep. 26, 2023

(54) ARTHROSCOPIC DEVICES AND METHODS

(71) Applicant: Relign Corporation, Campbell, CA (US)

(72) Inventors: Aaron Germain, San Jose, CA (US); Jan Echeverry, San Jose, CA (US); Jeff Norton, Emerald Hills, CA (US)

(73) Assignee: Relign Corporation, Campbell, CA (US)

( * ) Notice: Subject to any disclaimer, the term of this patent is extended or adjusted under 35 U.S.C. 154(b) by 437 days.

(21) Appl. No.: 17/143,739

(22) Filed: Jan. 7, 2021

(65) Prior Publication Data

US 2021/0177493 A1 Jun. 17, 2021

Related U.S. Application Data

(63) Continuation of application No. 15/633,372, filed on Jun. 26, 2017, now abandoned.

(51) Int. Cl.
*A61B 18/14* (2006.01)
*A61B 17/16* (2006.01)
(Continued)

(52) U.S. Cl.
CPC ........ *A61B 18/148* (2013.01); *A61B 17/1617* (2013.01); *A61B 17/32002* (2013.01); *A61B 18/14* (2013.01); *A61B 18/1482* (2013.01); *A61B 2017/0046* (2013.01); *A61B 2017/00398* (2013.01); *A61B 2017/00477* (2013.01); *A61B 2018/0091* (2013.01);
(Continued)

(58) Field of Classification Search
CPC ... A61B 18/148; A61B 18/14; A61B 18/1482; A61B 17/1617; A61B 17/32002
See application file for complete search history.

(56) References Cited

U.S. PATENT DOCUMENTS

| 3,628,865 A | 12/1971 | Spence-bate et al. |
| 3,903,891 A | 9/1975 | Brayshaw |

(Continued)

FOREIGN PATENT DOCUMENTS

| CN | 1977194 A | 6/2007 |
| CN | 101015474 A | 8/2007 |

(Continued)

OTHER PUBLICATIONS

"International Application Serial No. PCT US2017 039326, International Preliminary Report on Patentability dated Jan. 10, 2019", 12 pgs.

(Continued)

*Primary Examiner* — Joanne M Rodden
*Assistant Examiner* — Sean W Collins
(74) *Attorney, Agent, or Firm* — SCHWEGMAN LUNDBERG & WOESSNER, P.A.

(57) ABSTRACT

An arthroscopy system includes both a motorized handpiece and a detachable probe. The motorized handpiece includes a rotating driver which is configured to engage a rotatable drive coupling within a hub of the probe. The probe has a shaft with an articulating distal region, and the rotatable drive coupling is configured to convert the rotary motion of the rotating driver to an articulating motion within the articulating region of the probe.

22 Claims, 7 Drawing Sheets

Related U.S. Application Data

(60) Provisional application No. 62/357,786, filed on Jul. 1, 2016.

(51) Int. Cl.
*A61B 17/32* (2006.01)
*A61B 17/00* (2006.01)
*A61B 18/00* (2006.01)

(52) U.S. Cl.
CPC .............. *A61B 2018/00172* (2013.01); *A61B 2018/00577* (2013.01); *A61B 2018/1495* (2013.01)

(56) References Cited

U.S. PATENT DOCUMENTS

| | | |
|---|---|---|
| 4,428,748 A | 1/1984 | Peyman et al. |
| 4,949,718 A | 8/1990 | Neuwirth et al. |
| 4,979,948 A | 12/1990 | Geddes et al. |
| 5,045,056 A | 9/1991 | Behl |
| 5,078,717 A | 1/1992 | Parins et al. |
| 5,084,044 A | 1/1992 | Quint |
| 5,085,659 A | 2/1992 | Rydell |
| 5,191,883 A | 3/1993 | Lennox et al. |
| 5,197,963 A | 3/1993 | Parins |
| 5,242,390 A | 9/1993 | Goldrath |
| 5,248,312 A | 9/1993 | Langberg |
| 5,269,794 A | 12/1993 | Rexroth |
| 5,277,201 A | 1/1994 | Stern |
| 5,282,799 A | 2/1994 | Rydell |
| 5,324,254 A | 6/1994 | Phillips |
| 5,344,435 A | 9/1994 | Turner et al. |
| 5,374,261 A | 12/1994 | Yoon |
| 5,401,272 A | 3/1995 | Perkins |
| 5,401,274 A | 3/1995 | Kusunoki |
| 5,429,136 A | 7/1995 | Milo et al. |
| 5,441,498 A | 8/1995 | Perkins |
| 5,443,470 A | 8/1995 | Stern et al. |
| 5,454,787 A * | 10/1995 | Lundquist .......... A61B 10/0275 604/95.01 |
| 5,456,689 A | 10/1995 | Kresch et al. |
| 5,496,314 A | 3/1996 | Eggers |
| 5,501,681 A | 3/1996 | Neuwirth et al. |
| 5,505,730 A | 4/1996 | Edwards |
| 5,507,725 A | 4/1996 | Savage et al. |
| 5,558,672 A | 9/1996 | Edwards et al. |
| 5,562,703 A | 10/1996 | Desai |
| 5,562,720 A | 10/1996 | Stern et al. |
| 5,575,788 A | 11/1996 | Baker et al. |
| 5,584,872 A | 12/1996 | Lafontaine et al. |
| 5,592,727 A | 1/1997 | Glowa et al. |
| 5,622,647 A | 4/1997 | Kerr et al. |
| 5,647,848 A | 7/1997 | Slashed |
| 5,653,684 A | 8/1997 | Laptewicz et al. |
| 5,653,692 A | 8/1997 | Masterson et al. |
| 5,662,647 A | 9/1997 | Crow et al. |
| 5,672,174 A | 9/1997 | Gough et al. |
| 5,681,308 A | 10/1997 | Edwards et al. |
| 5,697,281 A | 12/1997 | Eggers et al. |
| 5,697,882 A | 12/1997 | Eggers et al. |
| 5,713,942 A | 2/1998 | Stern et al. |
| 5,733,298 A | 3/1998 | Berman et al. |
| 5,769,846 A | 6/1998 | Edwards et al. |
| 5,769,880 A | 6/1998 | Truckai et al. |
| 5,779,662 A | 7/1998 | Berman |
| 5,800,493 A | 9/1998 | Stevens et al. |
| 5,810,802 A | 9/1998 | Panescu et al. |
| 5,827,273 A | 10/1998 | Edwards |
| 5,843,020 A | 12/1998 | Tu et al. |
| 5,846,239 A | 12/1998 | Swanson et al. |
| 5,860,974 A | 1/1999 | Abele |
| 5,866,082 A | 2/1999 | Hatton et al. |
| 5,876,340 A | 3/1999 | Tu et al. |
| 5,879,347 A | 3/1999 | Saadat |
| 5,891,094 A | 4/1999 | Masterson et al. |
| 5,891,134 A | 4/1999 | Goble et al. |
| 5,891,136 A | 4/1999 | McGee et al. |
| 5,902,251 A | 5/1999 | Vanhooydonk et al. |
| 5,904,651 A | 5/1999 | Swanson et al. |
| 5,925,038 A | 7/1999 | Panescu et al. |
| 5,954,714 A | 9/1999 | Saadat et al. |
| 5,964,755 A | 10/1999 | Edwards |
| 5,976,129 A | 11/1999 | Desai |
| 5,980,515 A | 11/1999 | Tu |
| 5,997,534 A | 12/1999 | Tu et al. |
| 6,024,743 A | 2/2000 | Edwards |
| 6,026,331 A | 2/2000 | Feldberg et al. |
| 6,037,724 A | 3/2000 | Buss et al. |
| 6,041,260 A | 3/2000 | Stern et al. |
| 6,053,909 A | 4/2000 | Shadduck |
| 6,057,689 A | 5/2000 | Saadat |
| 6,086,581 A | 7/2000 | Reynolds et al. |
| 6,091,993 A | 7/2000 | Bouchier et al. |
| 6,113,597 A | 9/2000 | Eggers et al. |
| 6,136,014 A | 10/2000 | Sirimanne et al. |
| 6,139,570 A | 10/2000 | Saadat et al. |
| 6,146,378 A | 11/2000 | Mikus et al. |
| 6,149,620 A | 11/2000 | Baker et al. |
| 6,214,003 B1 | 4/2001 | Morgan et al. |
| 6,228,078 B1 | 5/2001 | Eggers et al. |
| 6,254,599 B1 | 7/2001 | Lesh et al. |
| 6,283,962 B1 | 9/2001 | Tu et al. |
| 6,296,639 B1 | 10/2001 | Truckai et al. |
| 6,302,904 B1 | 10/2001 | Wallsten et al. |
| 6,315,776 B1 | 11/2001 | Edwards et al. |
| 6,366,818 B1 | 4/2002 | Bolmsjo |
| 6,387,088 B1 | 5/2002 | Shattuck et al. |
| 6,395,012 B1 | 5/2002 | Yoon |
| 6,409,722 B1 | 6/2002 | Hoey et al. |
| 6,416,508 B1 | 7/2002 | Eggers et al. |
| 6,416,511 B1 | 7/2002 | Lesh et al. |
| 6,443,947 B1 | 9/2002 | Marko et al. |
| 6,491,690 B1 | 12/2002 | Goble et al. |
| 6,508,815 B1 | 1/2003 | Strul et al. |
| 6,551,310 B1 | 4/2003 | Ganz et al. |
| 6,565,561 B1 | 5/2003 | Goble et al. |
| 6,589,237 B2 | 7/2003 | Woloszko et al. |
| 6,602,248 B1 | 8/2003 | Sharps et al. |
| 6,607,545 B2 | 8/2003 | Kammerer et al. |
| 6,622,731 B2 | 9/2003 | Daniel et al. |
| 6,635,054 B2 | 10/2003 | Fjield et al. |
| 6,635,055 B1 | 10/2003 | Cronin |
| 6,663,626 B2 | 12/2003 | Truckai et al. |
| 6,673,071 B2 | 1/2004 | Vandusseldorp et al. |
| 6,699,241 B2 | 3/2004 | Rappaport et al. |
| 6,726,684 B1 | 4/2004 | Woloszko et al. |
| 6,736,811 B2 | 5/2004 | Panescu et al. |
| 6,746,447 B2 | 6/2004 | Davison et al. |
| 6,758,847 B2 | 7/2004 | Maguire |
| 6,780,178 B2 | 8/2004 | Palanker et al. |
| 6,802,839 B2 | 10/2004 | Behl |
| 6,813,520 B2 | 11/2004 | Truckai et al. |
| 6,814,730 B2 | 11/2004 | Li |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,872,205 B2 | 3/2005 | Lesh et al. |
| 6,896,674 B1 | 5/2005 | Woloszko et al. |
| 6,905,497 B2 | 6/2005 | Truckai et al. |
| 6,923,805 B1 | 8/2005 | Lafontaine et al. |
| 6,929,642 B2 | 8/2005 | Xiao et al. |
| 6,949,096 B2 | 9/2005 | Davison et al. |
| 6,951,569 B2 | 10/2005 | Nohilly |
| 6,954,977 B2 | 10/2005 | Maguire et al. |
| 6,960,203 B2 | 11/2005 | Xiao et al. |
| 7,074,217 B2 | 7/2006 | Strul et al. |
| 7,083,614 B2 | 8/2006 | Fjield et al. |
| 7,087,052 B2 | 8/2006 | Sampson et al. |
| 7,108,696 B2 | 9/2006 | Daniel et al. |
| 7,118,590 B1 | 10/2006 | Cronin |
| 7,150,747 B1 | 12/2006 | McDonald et al. |
| 7,175,734 B2 | 2/2007 | Stewart et al. |
| 7,179,255 B2 | 2/2007 | Lettice et al. |

(56) References Cited

U.S. PATENT DOCUMENTS

| | | |
|---|---|---|
| 7,186,234 B2 | 3/2007 | Dahla et al. |
| 7,192,430 B2 | 3/2007 | Truckai et al. |
| 7,238,185 B2 | 7/2007 | Palanker et al. |
| 7,270,658 B2 | 9/2007 | Woloszko et al. |
| 7,276,063 B2 | 10/2007 | Davison et al. |
| 7,278,994 B2 | 10/2007 | Goble |
| 7,294,126 B2 | 11/2007 | Sampson et al. |
| 7,297,143 B2 | 11/2007 | Woloszko et al. |
| 7,326,201 B2 | 2/2008 | Fjield et al. |
| 7,331,957 B2 | 2/2008 | Woloszko et al. |
| RE40,156 E | 3/2008 | Sharps et al. |
| 7,371,231 B2 | 5/2008 | Rioux et al. |
| 7,371,235 B2 | 5/2008 | Thompson et al. |
| 7,381,208 B2 | 6/2008 | Van et al. |
| 7,387,628 B1 | 6/2008 | Behl et al. |
| 7,390,330 B2 | 6/2008 | Harp |
| 7,407,502 B2 | 8/2008 | Strul et al. |
| 7,419,500 B2 | 9/2008 | Marko et al. |
| 7,452,358 B2 | 11/2008 | Stern et al. |
| 7,462,178 B2 | 12/2008 | Woloszko et al. |
| 7,500,973 B2 | 3/2009 | Vancelette et al. |
| 7,512,445 B2 | 3/2009 | Truckai et al. |
| 7,530,979 B2 | 5/2009 | Ganz et al. |
| 7,549,987 B2 | 6/2009 | Shadduck |
| 7,556,628 B2 | 7/2009 | Utley et al. |
| 7,566,333 B2 | 7/2009 | Van et al. |
| 7,572,251 B1 | 8/2009 | Davison et al. |
| 7,604,633 B2 | 10/2009 | Truckai et al. |
| 7,625,368 B2 | 12/2009 | Schechter et al. |
| 7,674,259 B2 | 3/2010 | Shadduck |
| 7,678,106 B2 | 3/2010 | Lee |
| 7,708,733 B2 | 5/2010 | Sanders et al. |
| 7,717,909 B2 | 5/2010 | Strul et al. |
| 7,736,362 B2 | 6/2010 | Eberl et al. |
| 7,744,595 B2 | 6/2010 | Truckai et al. |
| 7,749,159 B2 | 7/2010 | Crowley et al. |
| 7,824,398 B2 | 11/2010 | Woloszko et al. |
| 7,824,405 B2 | 11/2010 | Woloszko et al. |
| 7,846,160 B2 | 12/2010 | Payne et al. |
| 7,879,034 B2 | 2/2011 | Woloszko et al. |
| 7,918,795 B2 | 4/2011 | Grossman |
| 7,985,188 B2 | 7/2011 | Felts et al. |
| 8,012,153 B2 | 9/2011 | Woloszko et al. |
| 8,197,476 B2 | 6/2012 | Truckai |
| 8,197,477 B2 | 6/2012 | Truckai |
| 8,323,280 B2 | 12/2012 | Germain et al. |
| 8,372,068 B2 | 2/2013 | Truckai |
| 8,382,753 B2 | 2/2013 | Truckai |
| 8,486,096 B2 | 7/2013 | Robertson et al. |
| 8,500,732 B2 | 8/2013 | Truckai et al. |
| 8,540,708 B2 | 9/2013 | Truckai et al. |
| 8,657,174 B2 | 2/2014 | Yates et al. |
| 8,690,873 B2 | 4/2014 | Truckai et al. |
| 8,702,702 B1 | 4/2014 | Edwards et al. |
| 8,821,486 B2 | 9/2014 | Toth et al. |
| 8,998,901 B2 | 4/2015 | Truckai et al. |
| 9,204,918 B2 | 12/2015 | Germain et al. |
| 9,277,954 B2 | 3/2016 | Germain et al. |
| 9,427,249 B2 | 8/2016 | Robertson et al. |
| 9,472,382 B2 | 10/2016 | Jacofsky |
| 9,510,897 B2 | 12/2016 | Truckai |
| 9,585,675 B1 | 3/2017 | Germain et al. |
| 9,592,085 B2 | 3/2017 | Germain et al. |
| 9,603,656 B1 | 3/2017 | Germain et al. |
| 9,649,125 B2 | 5/2017 | Truckai |
| 9,662,163 B2 | 5/2017 | Toth et al. |
| 9,855,675 B1 | 1/2018 | Germain et al. |
| 9,901,394 B2 | 2/2018 | Shadduck et al. |
| 10,052,149 B2 | 8/2018 | Germain et al. |
| 10,213,246 B2 | 2/2019 | Toth et al. |
| 10,595,889 B2 | 3/2020 | Germain et al. |
| 10,675,087 B2 | 6/2020 | Truckai et al. |
| 2002/0022870 A1 | 2/2002 | Truckai et al. |
| 2002/0058933 A1 | 5/2002 | Christopherson et al. |
| 2002/0062142 A1 | 5/2002 | Knowlton |
| 2002/0068934 A1 | 6/2002 | Edwards et al. |
| 2002/0082635 A1 | 6/2002 | Kammerer et al. |
| 2002/0183742 A1 | 12/2002 | Carmel et al. |
| 2003/0060813 A1 | 3/2003 | Loeb et al. |
| 2003/0065321 A1 | 4/2003 | Carmel et al. |
| 2003/0130655 A1 | 7/2003 | Woloszko et al. |
| 2003/0153905 A1 | 8/2003 | Edwards et al. |
| 2003/0171743 A1 | 9/2003 | Tasto et al. |
| 2003/0176816 A1 | 9/2003 | Maguire et al. |
| 2003/0208200 A1 | 11/2003 | Palanker et al. |
| 2003/0216725 A1 | 11/2003 | Woloszko et al. |
| 2003/0236487 A1 | 12/2003 | Knowlton |
| 2004/0002702 A1 | 1/2004 | Xiao et al. |
| 2004/0010249 A1 | 1/2004 | Truckai et al. |
| 2004/0087936 A1 | 5/2004 | Stern et al. |
| 2004/0092980 A1 | 5/2004 | Cesarini et al. |
| 2004/0102770 A1 | 5/2004 | Goble |
| 2004/0215180 A1 | 10/2004 | Starkebaum et al. |
| 2004/0215182 A1 | 10/2004 | Lee |
| 2004/0215296 A1 | 10/2004 | Ganz et al. |
| 2004/0230190 A1 | 11/2004 | Dahla et al. |
| 2005/0075630 A1 | 4/2005 | Truckai et al. |
| 2005/0165389 A1 | 7/2005 | Swain et al. |
| 2005/0182397 A1 | 8/2005 | Ryan |
| 2005/0192652 A1 | 9/2005 | Cioanta et al. |
| 2005/0228372 A1 | 10/2005 | Truckai et al. |
| 2005/0240176 A1 | 10/2005 | Oral et al. |
| 2005/0251131 A1 | 11/2005 | Lesh |
| 2006/0009756 A1 | 1/2006 | Francischelli et al. |
| 2006/0052771 A1 | 3/2006 | Sartor et al. |
| 2006/0084158 A1 | 4/2006 | Viol |
| 2006/0084969 A1 | 4/2006 | Truckai et al. |
| 2006/0089637 A1 | 4/2006 | Werneth et al. |
| 2006/0178670 A1 | 8/2006 | Woloszko et al. |
| 2006/0189971 A1 | 8/2006 | Tasto et al. |
| 2006/0189976 A1 | 8/2006 | Kami et al. |
| 2006/0200040 A1 | 9/2006 | Weikel et al. |
| 2006/0224154 A1 | 10/2006 | Shadduck et al. |
| 2006/0259025 A1 | 11/2006 | Dahla |
| 2007/0021743 A1 | 1/2007 | Rioux et al. |
| 2007/0027447 A1 | 2/2007 | Theroux et al. |
| 2007/0083192 A1 | 4/2007 | Welch |
| 2007/0161981 A1 | 7/2007 | Sanders et al. |
| 2007/0213704 A1 | 9/2007 | Truckai et al. |
| 2007/0276430 A1 | 11/2007 | Lee et al. |
| 2007/0282323 A1 | 12/2007 | Woloszko et al. |
| 2007/0287996 A1 | 12/2007 | Rioux |
| 2007/0288075 A1 | 12/2007 | Dowlatshahi |
| 2007/0293853 A1 | 12/2007 | Truckai et al. |
| 2008/0058797 A1 | 3/2008 | Rioux |
| 2008/0097242 A1 | 4/2008 | Cai |
| 2008/0097425 A1 | 4/2008 | Truckai |
| 2008/0125765 A1 | 5/2008 | Berenshteyn et al. |
| 2008/0125770 A1 | 5/2008 | Kleyman |
| 2008/0154238 A1 | 6/2008 | McGuckin |
| 2008/0183132 A1 | 7/2008 | Davies et al. |
| 2008/0208189 A1 | 8/2008 | Van et al. |
| 2008/0221567 A1 | 9/2008 | Sixto et al. |
| 2008/0249518 A1 | 10/2008 | Warnking et al. |
| 2008/0249533 A1 | 10/2008 | Godin |
| 2008/0249553 A1 | 10/2008 | Gruber et al. |
| 2008/0281317 A1 | 11/2008 | Gobel |
| 2009/0048593 A1 | 2/2009 | Ganz et al. |
| 2009/0054888 A1 | 2/2009 | Cronin |
| 2009/0054892 A1 | 2/2009 | Dicarlo et al. |
| 2009/0076494 A1 | 3/2009 | Azure |
| 2009/0105703 A1 | 4/2009 | Shadduck |
| 2009/0131927 A1 | 5/2009 | Kastelein et al. |
| 2009/0149846 A1 | 6/2009 | Hoey et al. |
| 2009/0163908 A1 | 6/2009 | MacLean et al. |
| 2009/0209956 A1 | 8/2009 | Marion |
| 2009/0270899 A1 | 10/2009 | Carusillo et al. |
| 2009/0306654 A1 | 12/2009 | Garbagnati |
| 2010/0004595 A1 | 1/2010 | Nguyen et al. |
| 2010/0036372 A1 | 2/2010 | Truckai et al. |
| 2010/0042095 A1 | 2/2010 | Bigley et al. |
| 2010/0042097 A1 | 2/2010 | Taylor et al. |
| 2010/0049190 A1 | 2/2010 | Long et al. |
| 2010/0094289 A1 | 4/2010 | Taylor et al. |

(56) References Cited

U.S. PATENT DOCUMENTS

| | | |
|---|---|---|
| 2010/0100091 A1 | 4/2010 | Truckai |
| 2010/0100094 A1 | 4/2010 | Truckai |
| 2010/0106152 A1 | 4/2010 | Truckai et al. |
| 2010/0114089 A1 | 5/2010 | Truckai et al. |
| 2010/0121319 A1 | 5/2010 | Chu et al. |
| 2010/0125269 A1 | 5/2010 | Emmons et al. |
| 2010/0137855 A1 | 6/2010 | Berjano et al. |
| 2010/0137857 A1 | 6/2010 | Shroff et al. |
| 2010/0152725 A1 | 6/2010 | Pearson et al. |
| 2010/0185191 A1 | 7/2010 | Carr et al. |
| 2010/0198214 A1 | 8/2010 | Layton, Jr. et al. |
| 2010/0204688 A1 | 8/2010 | Hoey et al. |
| 2010/0217245 A1 | 8/2010 | Prescott |
| 2010/0217256 A1 | 8/2010 | Strul et al. |
| 2010/0228239 A1 | 9/2010 | Freed |
| 2010/0228245 A1 | 9/2010 | Sampson et al. |
| 2010/0234867 A1 | 9/2010 | Himes |
| 2010/0286680 A1 | 11/2010 | Kleyman |
| 2010/0286688 A1 | 11/2010 | Hughett, Sr. et al. |
| 2011/0004205 A1 | 1/2011 | Chu et al. |
| 2011/0046513 A1 | 2/2011 | Hibner |
| 2011/0060391 A1 | 3/2011 | Unetich et al. |
| 2011/0112524 A1 | 5/2011 | Stern et al. |
| 2011/0196401 A1 | 8/2011 | Robertson et al. |
| 2011/0196403 A1 | 8/2011 | Robertson et al. |
| 2011/0282340 A1 | 11/2011 | Toth et al. |
| 2012/0041434 A1 | 2/2012 | Truckai |
| 2012/0041437 A1 | 2/2012 | Truckai |
| 2012/0130381 A1 | 5/2012 | Germain |
| 2012/0330292 A1 | 12/2012 | Shadduck et al. |
| 2013/0090642 A1 | 4/2013 | Shadduck et al. |
| 2013/0103021 A1 | 4/2013 | Germain et al. |
| 2013/0103032 A1 | 4/2013 | Beaven |
| 2013/0172870 A1 | 7/2013 | Germain et al. |
| 2013/0231652 A1 | 9/2013 | Germain et al. |
| 2013/0253498 A1 | 9/2013 | Germain et al. |
| 2013/0267937 A1 | 10/2013 | Shadduck et al. |
| 2013/0296847 A1 | 11/2013 | Germain et al. |
| 2013/0331833 A1 | 12/2013 | Bloom |
| 2013/0345705 A1 | 12/2013 | Truckai et al. |
| 2014/0012249 A1 | 1/2014 | Truckai et al. |
| 2014/0114300 A1 | 4/2014 | Orczy-timko et al. |
| 2014/0160015 A1 | 6/2014 | Ogawa et al. |
| 2014/0276719 A1* | 9/2014 | Parihar .......... A61B 34/30 606/1 |
| 2014/0303611 A1 | 10/2014 | Shadduck et al. |
| 2014/0324065 A1 | 10/2014 | Bek et al. |
| 2014/0336632 A1 | 11/2014 | Toth et al. |
| 2015/0053741 A1 | 2/2015 | Shelton, IV et al. |
| 2015/0073341 A1* | 3/2015 | Salahieh .......... A61B 1/00135 604/95.01 |
| 2015/0119795 A1 | 4/2015 | Germain et al. |
| 2015/0119916 A1 | 4/2015 | Dietz et al. |
| 2015/0173827 A1 | 6/2015 | Bloom et al. |
| 2015/0182281 A1 | 7/2015 | Truckai et al. |
| 2016/0051307 A1 | 2/2016 | West, Jr. |
| 2016/0066982 A1 | 3/2016 | Marczyk et al. |
| 2016/0095615 A1 | 4/2016 | Orczy-timko et al. |
| 2016/0113706 A1 | 4/2016 | Truckai et al. |
| 2016/0157916 A1 | 6/2016 | Germain et al. |
| 2016/0242844 A1 | 8/2016 | Orczy-Timko |
| 2016/0331443 A1* | 11/2016 | Phan .......... A61B 17/1671 |
| 2016/0346036 A1 | 12/2016 | Orczy-Timko et al. |
| 2016/0346037 A1 | 12/2016 | Truckai et al. |
| 2017/0202612 A1 | 7/2017 | Germain et al. |
| 2017/0215912 A1 | 8/2017 | Truckai |
| 2017/0224368 A1 | 8/2017 | Germain et al. |
| 2017/0231681 A1 | 8/2017 | Toth et al. |
| 2017/0258519 A1 | 9/2017 | Germain et al. |
| 2017/0290602 A1 | 10/2017 | Germain et al. |
| 2018/0000534 A1 | 1/2018 | Germain et al. |
| 2018/0242962 A1* | 8/2018 | Walen .......... A61B 1/0051 |
| 2019/0021788 A1 | 1/2019 | Germain et al. |

FOREIGN PATENT DOCUMENTS

| | | |
|---|---|---|
| CN | 101198288 A | 6/2008 |
| CN | 105228502 | 1/2016 |
| CN | 105658152 A | 6/2016 |
| CN | 109661209 | 4/2019 |
| EP | 1236440 A1 | 9/2002 |
| EP | 1595507 A2 | 11/2005 |
| EP | 2349044 A1 | 8/2011 |
| EP | 2493407 A1 | 9/2012 |
| EP | 2772206 A2 | 9/2014 |
| EP | 2981222 A1 | 2/2016 |
| EP | 3478197 | 5/2019 |
| JP | 2005501597 A | 1/2005 |
| JP | 2010505521 | 2/2010 |
| JP | 2013103137 | 5/2013 |
| JP | 2019524202 | 9/2019 |
| WO | WO-9624296 A1 | 8/1996 |
| WO | WO-0053112 A2 | 9/2000 |
| WO | WO-2005122938 A1 | 12/2005 |
| WO | WO-2006001455 A1 | 1/2006 |
| WO | WO-2008083407 A1 | 7/2008 |
| WO | WO-2010048007 A1 | 4/2010 |
| WO | WO-2011053599 A1 | 5/2011 |
| WO | WO-2011060301 A1 | 5/2011 |
| WO | WO-2013009252 A2 | 1/2013 |
| WO | WO-2013067417 A1 | 5/2013 |
| WO | WO-2014165715 A1 | 10/2014 |
| WO | WO-2015026644 A1 | 2/2015 |
| WO | WO-2016171963 A1 | 10/2016 |
| WO | WO-2016175980 A1 | 11/2016 |
| WO | WO-2017127760 A1 | 7/2017 |
| WO | WO-2017185097 A1 | 10/2017 |
| WO | WO-2018005382 A1 | 1/2018 |

OTHER PUBLICATIONS

"European Application Serial No. 17821026.6, Response to Communication pursuant to Rules 161(1) and 162 EPC filed Mar. 7, 2019", 8 pgs.

"European Application Serial No. 17821026.6, Response filed Nov. 2, 2020 to Extended European Search Report dated Mar. 31, 2020", 8 pgs.

"Chinese Application Serial No. 201780053916.5, Notification of Paying the Restoration Fee mailed Nov. 13, 2020", With English machine translation, 3 pgs.

"Chinese Application Serial No. 201780053916.5, Office Action dated Jan. 28, 2021", With English machine translation, 3 pgs.

"Japanese Application Serial No. 2018-568311, Notification of Reasons for Rejection dated Apr. 27, 2021", With English machine translation, 14 pgs.

"Japanese Application Serial No. 2018-568311, Amendment filed May 29, 2021", w English Translation, 5 pgs.

"Japanese Application Serial No. 2018-568311, Amendment filed Jun. 2, 2020", w English Translation, 5 pgs.

"Chinese Application Serial No. 201780053916.5, Office Action dated Jun. 1, 2021", With English translation, 14 pgs.

"Japanese Application Serial No. 2018-568311, Response filed Aug. 20, 2021 to Notification of Reasons for Rejection dated Apr. 27, 2021", w English claims, 6 pgs.

"U.S. Appl. No. 12/541,043, Final Office Action dated Sep. 28, 2012", 6 pgs.

"U.S. Appl. No. 12/541,043, Non Final Office Action dated Mar. 12, 2012", 12 pgs.

"U.S. Appl. No. 12/541,043, Notice of Allowance dated Nov. 15, 2012".

"U.S. Appl. No. 12/541,050, Final Office Action dated Sep. 28, 2012", 6 pgs.

"U.S. Appl. No. 12/541,050, Non Final Office Action dated Mar. 12, 2012", 9 pgs.

"U.S. Appl. No. 12/541,050, Notice of Allowance dated Nov. 15, 2012".

"U.S. Appl. No. 12/605,546, Final Office Action dated Jan. 28, 2013", 7 pgs.

(56) References Cited

OTHER PUBLICATIONS

"U.S. Appl. No. 12/605,546, Non Final Office Action dated Jun. 18, 2012", 22 pgs.
"U.S. Appl. No. 12/605,546, Notice of Allowance dated Mar. 29, 2013", 6 pgs.
"U.S. Appl. No. 12/605,929, Non Final Office Action dated Sep. 28, 2012", 12 pgs.
"U.S. Appl. No. 12/605,929, Notice of Allowance dated May 24, 2013", 8 pgs.
"U.S. Appl. No. 12/944,466, Notice of Allowance dated May 9, 2014", 9 pgs.
"U.S. Appl. No. 13/236,471, Final Office Action dated Jul. 5, 2016", 14 pgs.
"U.S. Appl. No. 13/236,471, Non Final Office Action dated Sep. 24, 2015", 15 pgs.
"U.S. Appl. No. 13/236,471, Non Final Office Action dated Dec. 4, 2014", 16 pgs.
"U.S. Appl. No. 13/236,471, Notice of Allowance dated Jan. 27, 2017", 7 pgs.
"U.S. Appl. No. 13/281,805, Final Office Action dated Mar. 31, 2016", 9 pgs.
"U.S. Appl. No. 13/281,805, Final Office Action dated Dec. 16, 2014", 11 pgs.
"U.S. Appl. No. 13/281,805, Non Final Office Action dated Jul. 23, 2015", 9 pgs.
"U.S. Appl. No. 13/281,805, Non Final Office Action dated Sep. 22, 2014", 11 pgs.
"U.S. Appl. No. 13/281,805, Notice of Allowance dated Aug. 2, 2016", 11 pgs.
"U.S. Appl. No. 13/281,846, Non Final Office Action dated Dec. 6, 2011", 11 pgs.
"U.S. Appl. No. 13/281,846, Notice of Allowance dated Mar. 5, 2012", 7 pgs.
"U.S. Appl. No. 13/281,856, Non Final Office Action dated Dec. 22, 2011", 8 pgs.
"U.S. Appl. No. 13/281,856, Notice of Allowance dated Mar. 5, 2012", 7 pgs.
"U.S. Appl. No. 13/857,068, Final Office Action dated Feb. 4, 2016", 8 pgs.
"U.S. Appl. No. 13/857,068, Final Office Action dated Apr. 5, 2017", 12 pgs.
"U.S. Appl. No. 13/857,068, Non Final Office Action dated Jun. 5, 2015", 8 pgs.
"U.S. Appl. No. 13/857,068, Non Final Office Action dated Sep. 7, 2016", 11 pgs.
"U.S. Appl. No. 13/857,068, Non Final Office Action dated Oct. 9, 2014", 9 pgs.
"U.S. Appl. No. 13/857,068, Notice of Allowance dated Dec. 14, 2017", 7 pgs.
"U.S. Appl. No. 13/938,032, Non Final Office Action dated Nov. 6, 2013", 7 pgs.
"U.S. Appl. No. 13/938,032, Notice of Allowance dated Jan. 9, 2014", 5 pgs.
"U.S. Appl. No. 13/975,139, Final Office Action dated Oct. 24, 2014", 6 pgs.
"U.S. Appl. No. 13/975,139, Non Final Office Action dated Apr. 24, 2014", 9 pgs.
"U.S. Appl. No. 13/975,139, Notice of Allowance dated Feb. 25, 2015", 2 pgs.
"U.S. Appl. No. 13/975,139, Notice of Allowance dated Dec. 2, 2014", 6 pgs.
"U.S. Appl. No. 14/341,121, Final Office Action dated Jun. 28, 2018", 7 pgs.
"U.S. Appl. No. 14/341,121, Non Final Office Action dated Nov. 27, 2017", 10 pgs.
"U.S. Appl. No. 14/341,121, Notice of Allowance dated Oct. 19, 2018", 7 pgs.
"U.S. Appl. No. 14/341,121, Notice of Allowance dated Nov. 15, 2018", 4 pgs.
"U.S. Appl. No. 14/508,856, Non Final Office Action dated Jun. 29, 2016", 10 pgs.
"U.S. Appl. No. 14/508,856, Notice of Allowance dated Jan. 27, 2017", 10 pgs.
"U.S. Appl. No. 14/657,684, Final Office Action dated Apr. 18, 2017", 9 pgs.
"U.S. Appl. No. 14/657,684, Final Office Action dated Apr. 22, 2016", 9 pgs.
"U.S. Appl. No. 14/657,684, Non Final Office Action dated May 22, 2015", 7 pgs.
"U.S. Appl. No. 14/657,684, Non Final Office Action dated Jul. 12, 2018", 8 pgs.
"U.S. Appl. No. 14/657,684, Non Final Office Action dated Nov. 2, 2016", 9 pgs.
"U.S. Appl. No. 14/864,379, Final Office Action dated Jun. 15, 2018", 16 pgs.
"U.S. Appl. No. 14/864,379, Non Final Office Action dated Dec. 5, 2017", 12 pgs.
"U.S. Appl. No. 15/008,341, Non Final Office Action dated Jan. 2, 2019", 11 pgs.
"U.S. Appl. No. 15/091,402, Final Office Action dated Mar. 9, 2017", 16 pgs.
"U.S. Appl. No. 15/091,402, Final Office Action dated Mar. 14, 2018", 12 pgs.
"U.S. Appl. No. 15/091,402, Non Final Office Action dated Jul. 28, 2017", 13 pgs.
"U.S. Appl. No. 15/091,402, Non Final Office Action dated Sep. 30, 2016", 22 pgs.
"U.S. Appl. No. 15/091,402, Notice of Allowance dated Feb. 3, 2020", 6 pgs.
"U.S. Appl. No. 15/410,723, Final Office Action dated May 9, 2017", 12 pgs.
"U.S. Appl. No. 15/410,723, Non Final Office Action dated Mar. 14, 2017", 12 pgs.
"U.S. Appl. No. 15/410,723, Notice of Allowance dated Apr. 24, 2018", 8 pgs.
"U.S. Appl. No. 15/488,270, Non Final Office Action dated Feb. 19, 2019", 7 pgs.
"U.S. Appl. No. 15/583,712, Non Final Office Action dated Nov. 1, 2018", 9 pgs.
"U.S. Appl. No. 15/633,372, Final Office Action dated Dec. 26, 2019", 21 pgs.
"U.S. Appl. No. 15/633,372, Non Final Office Action dated May 2, 2019", 24 pgs.
"U.S. Appl. No. 15/633,372, Non Final Office Action dated Aug. 7, 2020", 22 pgs.
"U.S. Appl. No. 15/633,372, Response filed Mar. 6, 2019 to Restriction Requirement dated Jan. 25, 2019", 1 pg.
"U.S. Appl. No. 15/633,372, Response filed Jun. 16, 2020 to Final Office Action dated Dec. 26, 2019", 12 pgs.
"U.S. Appl. No. 15/633,372, Response filed Oct. 1, 2019 to Non Final Office Action dated May 2, 2019", 15 pgs.
"U.S. Appl. No. 15/633,372, Restriction Requirement dated Jan. 25, 2019", 5 pgs.
"Co-pending U.S. Appl. No. 15/495,620, filed Apr. 24, 2017".
"Co-pending U.S. Appl. No. 15/880,958, filed Jan. 26, 2018".
"European Application Serial No. 09822443, Extended European Search Report dated Apr. 16, 2013", 7 pgs.
"European Application Serial No. 10827399, Extended European Search Report dated Jul. 10, 2013", 6 pgs.
"European Application Serial No. 16786901.5, Extended European Search Report dated Nov. 19, 2018", 7 pgs.
"European Application Serial No. 17742070.0, Extended European Search Report dated May 23, 2019", 7 pgs.
"European Application Serial No. 17786807.2, Extended European Search Report dated Nov. 4, 2019", 7 pgs.
"European Application Serial No. 17821026.6, Extended European Search Report dated Mar. 31, 2020", 9 pgs.
"International Application Serial No. PCT/US2009/060703, International Search Report dated Dec. 10, 2009", 2 pgs.
"International Application Serial No. PCT/US2009/060703, Written Opinion dated Dec. 10, 2009", 6 pgs.

(56) References Cited

OTHER PUBLICATIONS

"International Application Serial No. PCT/US2010/054150, International Search Report dated Dec. 14, 2010", 2 pgs.
"International Application Serial No. PCT/US2010/054150, Written Opinion dated Dec. 14, 2010", 11 pgs.
"International Application Serial No. PCT/US2010/056591, International Search Report dated Feb. 2, 2011".
"International Application Serial No. PCT/US2010/056591, Written Opinion dated Feb. 2, 2011".
"International Application Serial No. PCT/US2014/032895, International Search Report dated Sep. 10, 2014", 2 pgs.
"International Application Serial No. PCT/US2016/025509, International Search Report dated Jul. 6, 2016", 2 pgs.
"International Application Serial No. PCT/US2017/014456, International Search Report dated May 31, 2017", 4 pgs.
"International Application Serial No. PCT/US2017/014456, Written Opinion dated May 31, 2017", 7 pgs.
"International Application Serial No. PCT/US2017/029201, International Search Report dated Jul. 7, 2017", 2 pgs.
"International Application Serial No. PCT/US2017/029201, Written Opinion dated Jul. 7, 2017", 6 pgs.
"International Application Serial No. PCT/US2017/039326, International Search Report dated Nov. 3, 2017", 4 pgs.
"International Application Serial No. PCT/US2017/039326, Written Opinion dated Nov. 3, 2017", 10 pgs.
Allen-Bradley, "AC Braking Basics", Web article, Rockwell Automation, Rockwell International Corporation, [Online]. Retrieved from the Internet: <http://literature.rockwellautomation.com/idc/groups/literature/documents/wp/drives-wp004_-enp.pdf>, (Feb. 2001), 4 pgs.
Allen-Bradley, "What is Regeneration? Braking / Regeneration Manual: Regeneration Overview", Revision 1.0. Rockwell Automation, [Online]. Retrieved from the Internet: <https://www.ab.com/supportlabdrives/documentation/techpapers/RegenOverview01.pdf> Accessed Apr. 24, 2017, 6 pgs.
Volpato, et al., "Application of Zirconia in Dentistry: Biological, Mechanical and Optical Considerations.", Advances in ceramics-electric and magnetic ceramics, bioceramics, ceramics and environment, (Sep. 2011), 397-420.

* cited by examiner

ARTHROSCOPIC DEVICES AND METHODS

CROSS-REFERENCE TO RELATED APPLICATIONS

This application claims the benefit of provisional application No. 62/357,786, filed on Jul. 1, 2016, the full disclosure of which is incorporated herein by reference.

BACKGROUND OF THE INVENTION

1. Field of the Invention

This invention relates to arthroscopic surgical devices by which anatomical tissues in knee joints, hip joints and the like may be ablated, cut and/or removed from a joint. More specifically, this invention relates to electrosurgical probes that can be articulated with a motor drive in an arthroscopy handpiece.

Arthroscopic joint and other procedures, such as hip treatments, subacromial decompression, treatment of the acromioclavicular joints, often require a number of different tools having different functions and structures. In order to reduce the cost and inventory burdens associated with using a large array of tools in a single procedure. "resposable" tools having a disposable working end and a reusable handpiece have been proposed. The handpiece will be designed to work with a large number of different tool types having different functions and "working ends" so that the cost and inventory of necessary tools can be reduced.

While the use of resposable tools holds great promise, a successful resposable tool system requires that one type of handpiece be compatible with as many types of tools and working ends as possible. For example, many handpieces will have motor drives with a rotating drive shaft. Such motor drives need to be compatible not only with rotating end effectors, such as drills, shavers, grinders, and the like, they should also be compatible with non-rotating end effectors.

Of particular interest to the present invention, it would be desirable to provide tools and working ends having articulating end effectors which can be driven by a motorized handpiece having a rotatable drive element. Arthroscopic probes having an articulating working end allow physicians to reach targeted tissues which would otherwise be difficult to access. The need thus exists for improved and alternative articulating arthroscopic devices that that can ablate and extract soft tissue rapidly and also be compatible with rotating drive elements. At least some of these objectives will be met by the inventions described and claimed herein.

2. Description of the Background Art

Arthroscopic tissue ablation and extraction devices are described in the following commonly owned patents and published applications: U.S. Pat. Nos. 9,603,656; 9,585,675; 9,592,085; 9,277,954; 9,204,918; and 8,323,280; and U.S. Patent Publication Nos. US 2016/0346036; US 2016/0157916; and US 2016/0113706, the full disclosures of which are incorporated herein by reference.

SUMMARY OF THE INVENTION

The present invention provides arthroscopic and other minimally invasive tools and tool systems. The tool systems include motorized handpieces and detachable tools, where the detachable tools are usually intended for only a single use by a single patient (often being referred to as disposable tools) and the motorized handpieces are usually intended to be reused in multiple procedures for multiple patients (often being referred to as "resposable"). The motorized handpieces will provide a rotating drive element or drive shaft which is configured to engage or mate with a rotatable coupling in or on the tool. The rotatable coupling, in turn, will be configured to convert the rotary motion of the drive shaft or driver into an articulating motion within a distal region of the tool. In this way, the "resposable" handpiece can be used with conventional rotary and other tools as well as with the particular tools of the present invention which have articulating regions as described in detail below.

In a first specific aspect, the present invention comprises a device intended for use with a motorized handpiece having a rotating driver. The device comprises a shaft having a proximal end and an articulating distal region. A hub is attached to the proximal end of the shaft, and the hub is adapted for or configured to detachably connect to the motorized handpiece. A rotatable drive coupling on or within the hub is configured to detachably engage the rotating driver when the hub is connected to the handpiece. In this way, rotation of the drive coupling by the driver causes the articulating distal region of the shaft to articulate.

In particular embodiments, the shaft of the device comprises outer and inner concentric or coaxial sleeves, where a proximal end of the outer sleeve is fixed in or to the hub and a proximal portion of the inner sleeve is axially movably or translatably mounted in an interior bore of the outer sleeve in response to rotation of the driver. Usually, the shaft will have at least one distal component that maintains the distal ends of the outer and inner sleeves in a fixed relationship. i.e., the distal component fixedly couples the two ends together. Typically, a threaded collar on a proximal end of the inner sleeve threadably engages the drive coupling to longitudinally drive the threaded collar as the rotatable drive coupling is rotated by the rotating driver of the handpiece.

In an alternative embodiment, the rotatable drive coupling can rotate in a first direction relative to a first collar fixed to a proximal end of the inner sleeve and rotation of the drive coupling rotates a pin thereon to engage against an engaging surface of the first collar to longitudinally drive the first collar to articulate the distal region of the shaft.

In still further embodiments, a reciprocatable electrode is disposed at a distal tip of the articulating distal region of the shaft and is carried by a third concentric sleeve having a distal end and a proximal end. The distal end of the third sleeve is attached to the reciprocatable electrode and proximal end is attached to the drive coupling. The rotatable drive coupling is configured to rotate in a second direction and rotation of the drive coupling and pin in the second direction against a cam surface on the first collar longitudinally drives the third sleeve to reciprocate the reciprocatable electrode.

In other specific embodiments, the at least one distal component at the distal end of the shaft is a ceramic member and carries at least one electrode, typically carrying at least a first polarity electrode and a distal region of the shaft comprises a second polarity electrode. In other specific embodiments, the articulating region of the shaft comprises a series of slots in the outer and/or inner sleeves. For example, slots in the outer sleeve may be radially offset from slots in the inner sleeve. By adjusting the degree of radial offset, the direction of deflection of the articulating distal region can be adjusted. In still other specific embodiments, an insulation layer may be disposed between the outer and inner sleeves, and first and second electrical contacts may be provided in the hub to connect respectively to first and second polarity electrodes on the shaft to provide for delivery of radio frequency (RF) current to the electrode(s).

The motorized handpiece will typically comprise a motor within a housing of the handpiece, and the housing will usually have one or more actuators for effecting various functions of the handpiece. In one example, an actuator on an outer surface of the handpiece provides for manually activating the motor to bend the articulating region. In another example, an actuator on an outer surface of the handpiece provides for controlling delivery of RF current to the first and second polarity electrodes.

In still further examples, the inner sleeve of the shaft may have an interior passageway extending to an open termination in a distal region of the shaft. The interior passageway is typically adapted to be connected to a negative pressure source in order to provide for aspiration through the tool and the handpiece when the handpiece is connected to the negative pressure source.

In a second specific aspect, an arthroscopy system comprises a motorized handpiece having a motor-driven driver or drive shaft. The system further comprises a probe having both (a) a proximal hub adapted for detachable connection to the motorized handpiece and (b) a probe shaft having an articulating distal region. A rotatable drive coupling disposed within the hub is adapted for coupling to the motor-driven driver or drive shaft, where rotation of the drive coupling by the driver will cause articulation of the articulating distal region.

In specific embodiments of the arthroscopy system, the shaft comprises outer and inner concentric sleeves, where a proximal end of the outer sleeve is fixed in or on the hub and a proximal end of the inner sleeve is fixed in the rotatable drive coupling. A proximal portion of the inner sleeve is typically axially or longitudinally moveable in an interior bore of the outer sleeve so that relative axial translation of the sleeves will cause articulation of the distal region. A ceramic member is typically used to connect the distal ends of the outer and inner sleeves, and first and/or second polarity electrodes may be carried on the ceramic member. An insulation layer may be disposed between the inner and outer sleeves, and electrical contacts on the handpiece are typically adapted for coupling with cooperating or corresponding electrical contacts in the hub to allow for energizing the first and second polarity electrodes.

The arthroscopy system may further comprise a reciprocatable electrode at a distal tip of the articulating distal region of the shaft carried by a third concentric sleeve having a distal end and a proximal end. The distal end is attached to the reciprocatable electrode, and the proximal end is driven by the rotatable drive coupling to longitudinally drive the third sleeve to reciprocate the reciprocatable electrode.

In a third specific aspect, the present invention provides an arthroscopy system comprising a motorized handpiece having a motor and a motor actuator button. A probe having a hub connected to a shaft having an articulating region is detachably connectible to the motorized handpiece. In particular, a hub is adapted for detachable connection to the motorized handpiece where a motor within the handpiece is configured to articulate the articulating region of the probe shaft. The actuator button and motor are configured or adapted to continuously articulate the articulating region when pressure is applied to the button to cause deformation of the articulating region between a linear shape or configuration and a fully articulated shape or configuration, or a release of pressure on the actuator button will stop such continuous articulation.

In a fourth aspect, an arthroscopy system comprises a motorized handpiece having a motor and a motor actuator button. A probe having a hub connected to a shaft has an articulating distal region. The hub is adapted for detachable connection to the motorized handpiece, and the motor and motor actuator button are configured to articulate the articulating region of the probe shaft such that pressure on the actuator button articulates the articulating region between a linear shape and a fully articulated shape.

In a fifth aspect of the present invention, an arthroscopy system comprises a motorized handpiece having a motor and a motor actuator button. A probe having a hub connected to a shaft has an articulating distal region. The hub is adapted for detachable connection to the motorized handpiece, and the motor and motor actuator button are configured to articulate the articulating region of the probe shaft such that pressure and release of pressure on the actuator button articulates the articulating region a selected number of degrees from a linear shape or configuration to a fully articulated shape or configuration.

In a sixth aspect, the present invention comprises an arthroscopy system including a motorized handpiece having a motor and at least one motor actuator button. A hub on a probe is adapted for a detachable connection to the motorized handpiece, and the motor and a motor actuator button are configured to articulate the articulating region of the probe shaft and to initiate or energize different modes of RF current delivery to bi-polar or other electrodes carried on the probe shaft. The RF current delivery mode may comprise an ablation wave form or a coagulation wave form for delivery of RF current to the electrodes.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to arthroscopy systems and related methods of use. Several variations of the invention will now be described to provide an overall understanding of the principles of the form, function and methods of use of the devices disclosed herein. In general, the present disclosure provides for an articulating arthroscopic system that includes a single-use articulating RF probe that can be detachable coupled to a re-usable motorized handpiece. This description of the general principles of this invention is not meant to limit the inventive concepts in the appended claims.

Figure 1:
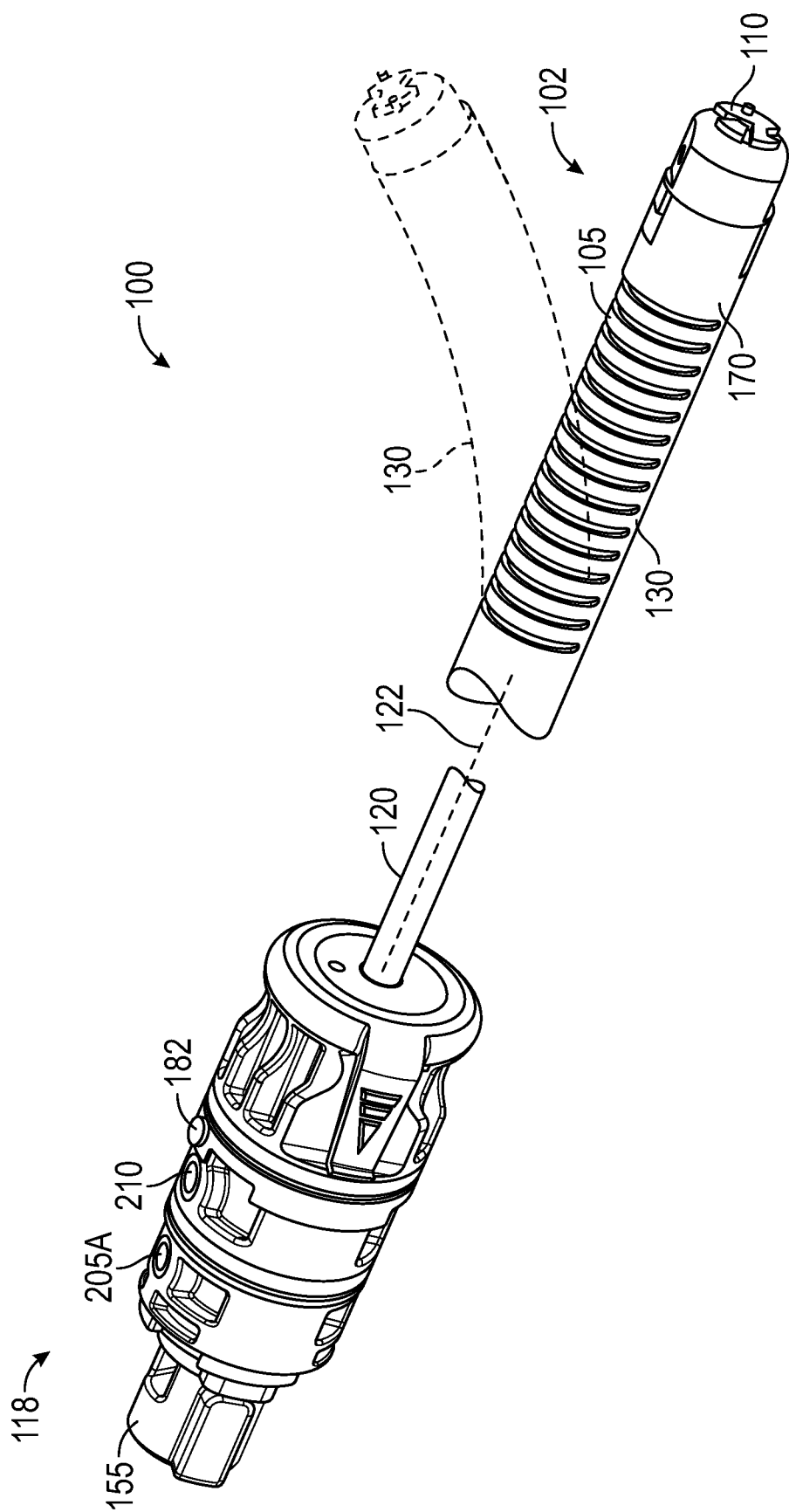
FIG. 1 is a perspective view of a disposable arthroscopic RF probe that has an articulating working end with a stationary active electrode, wherein the articulating mechanism is actuated by a motor drive in an arthroscopic handpiece.
Figure 2:
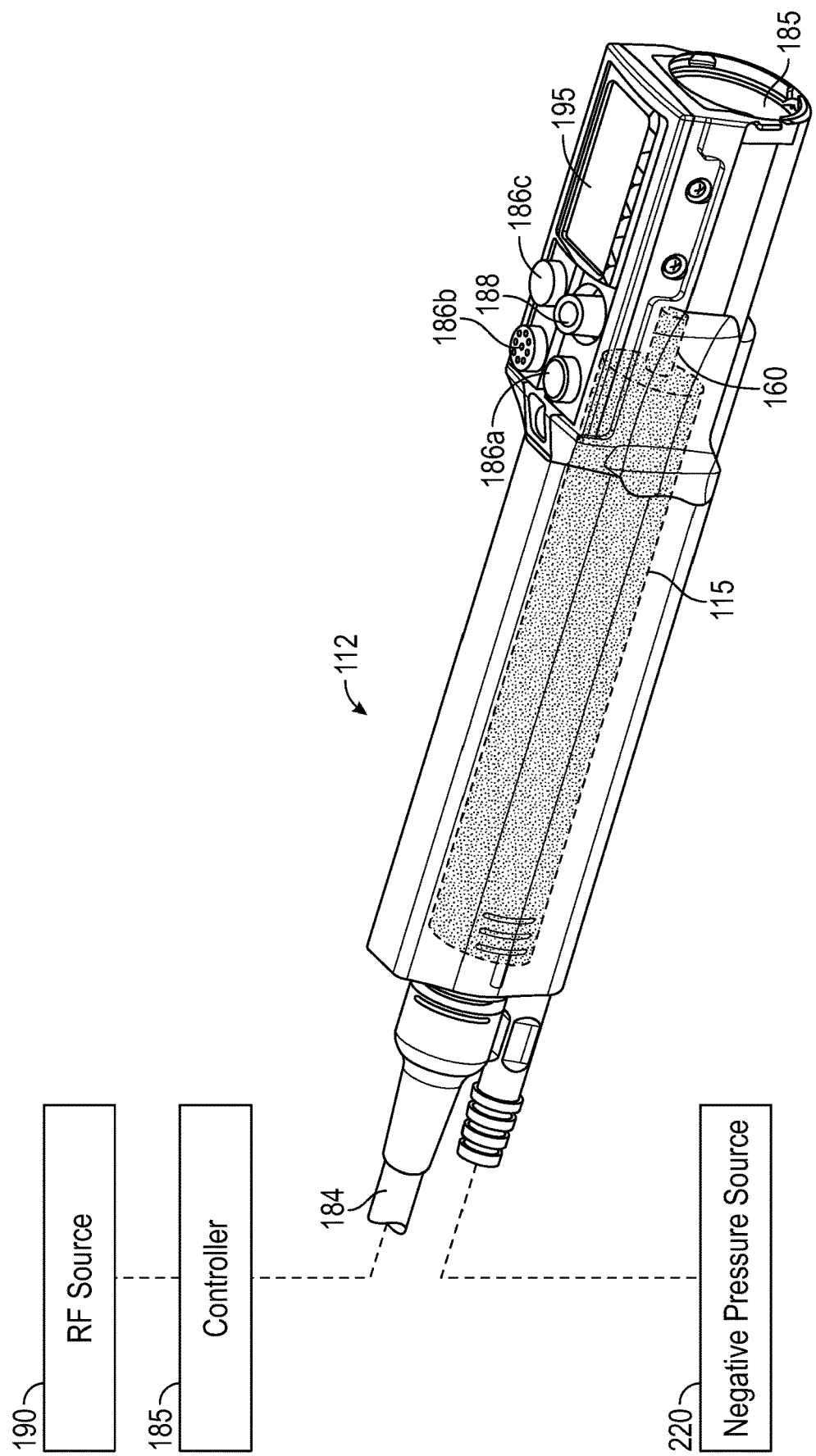
FIG. 2 is a perspective view of an arthroscopic handpiece with a motor drive that is used in combination with the RF probe of FIG. 1.

Referring now to the drawings and the reference numbers marked thereon. FIGS. 1 and 2 illustrate an arthroscopic system that is provided for treating joint tissue, wherein FIG. 1 shows a disposable articulating probe 100 with a working end 102 that has an articulating region 105 with a distal active electrode 110. FIG. 2 illustrates a reusable handle or handpiece 112 with a motor drive 115 carried therein, wherein the probe 100 of FIG. 1 is adapted for detachable coupling to the handpiece 112 of FIG. 2. The articulating working end 102 allows for selected articulation up to 90° or more to thus allow the physician to orient the distal electrode 110 as needed in a joint to ablate and/or smooth joint tissue, for example to treat damaged regions of an articular surface in a hip, knee, shoulder, ankle or other joint.

Figure 3A:
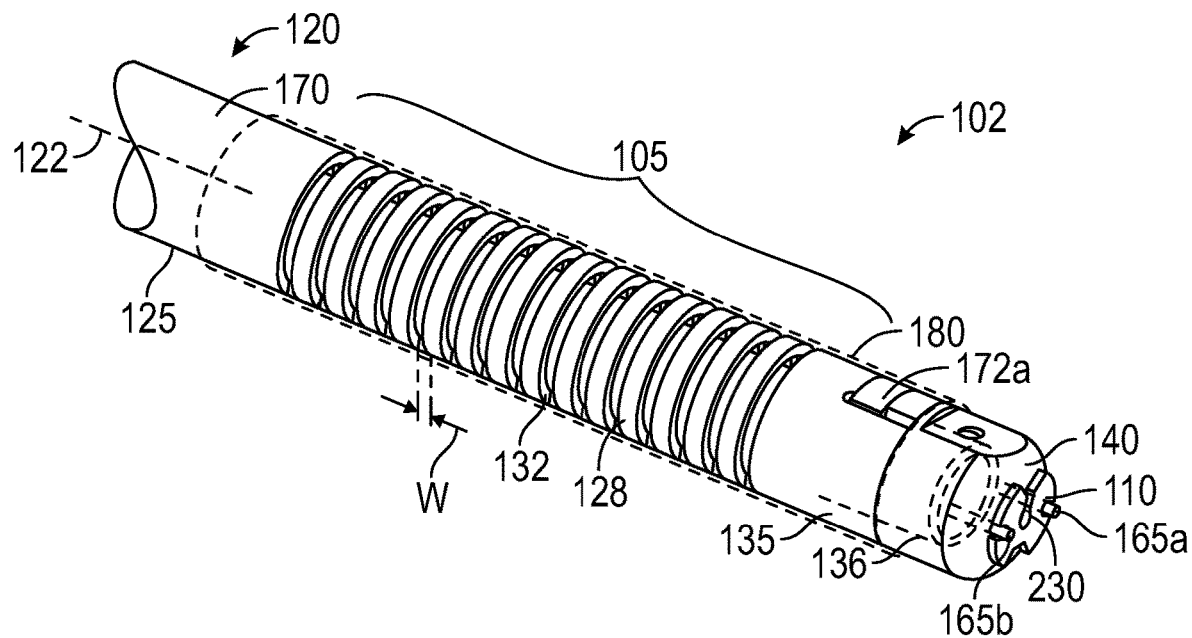
FIG. 3A is a perspective view of the articulating working end of the RF probe of FIG. 1 showing the RF electrodes.
Figure 3B:
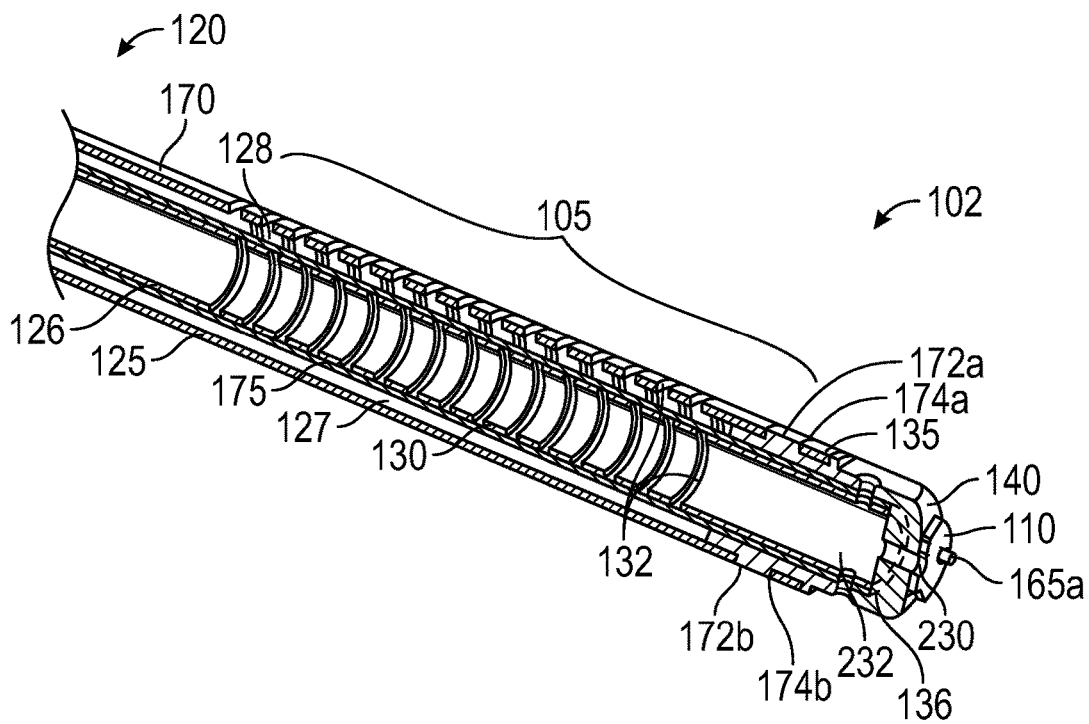
FIG. 3B is a sectional perspective view of the articulating working end FIG. 3A.
Figure 4:
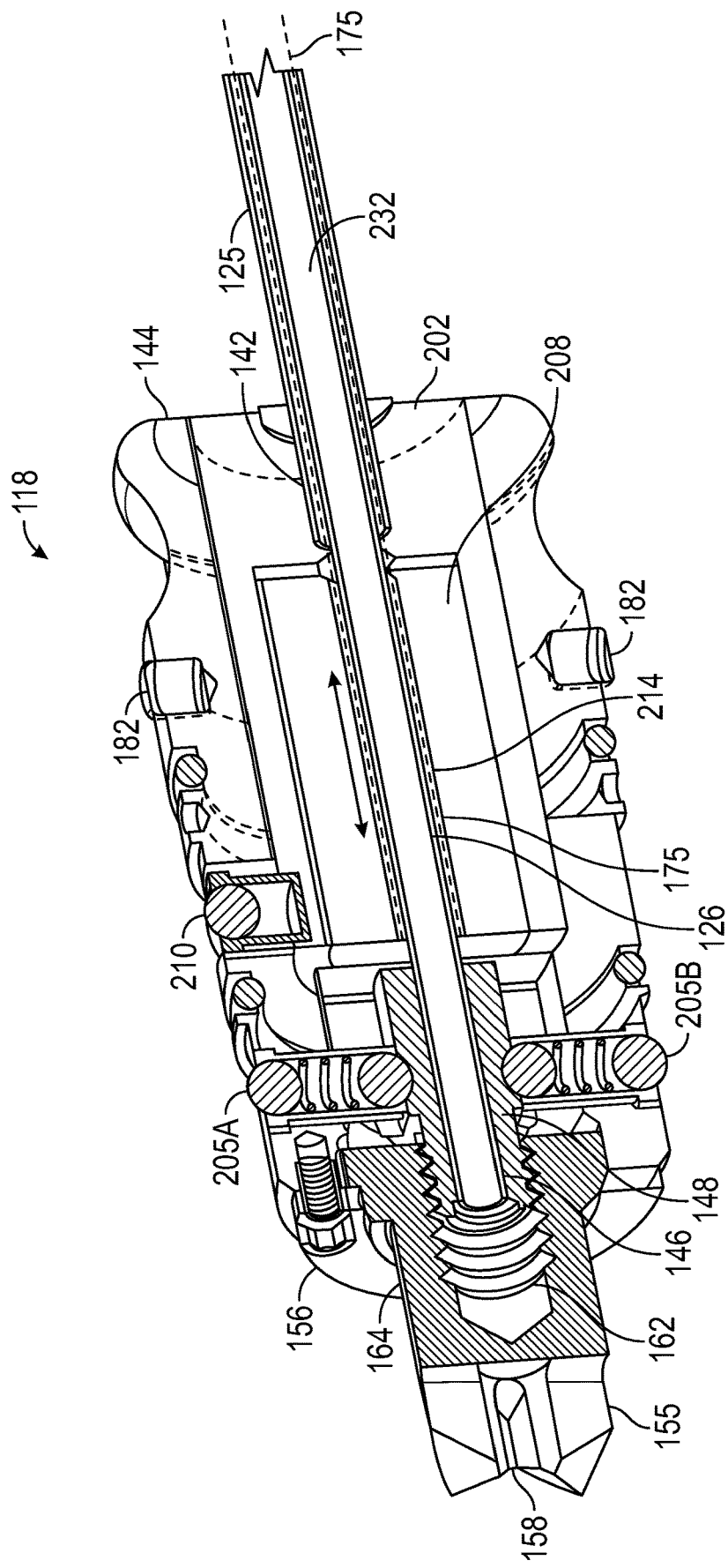
FIG. 4 is a sectional view of the proximal hub of the RF probe of FIG. 1 showing the motor driven articulation mechanism and the RF current carrying members.

More in particular, the articulating probe 100 as shown in FIG. 1 has a proximal hub assembly 118 that is connected to an elongate shaft 120 extending about longitudinal axis 122 to the distal working end 102. Referring to FIGS. 3A-3B and FIG. 4, the shaft 120 comprises an outer sleeve 125 and an inner sleeve 126 slidably disposed in bore 127 of the outer sleeve 125. The inner and outer sleeves 125 and 126 can be fabricated of a suitable metal alloy, such as stainless steel or NiTi. The wall thicknesses of the inner and outer sleeves 125, 126 can range from about 0.005" to 0.010" with the outer diameter the outer sleeve 125 ranging from about 2.0 mm to 6.0 mm.

FIGS. 3A-3B show the articulating region 105 of shaft 120 in more detail. In FIG. 3A, it can be seen that the outer sleeve 125 has a slotted region 128 that allows for its articulation. FIG. 3B shows that inner sleeve 126 has a similar slotted region 130 with the slots 132 in each sleeve rotationally offset from one another by 180°. In the variation of FIGS. 1 and 3A-3B, the inner and outer slotted sleeve portions 128 and 130 can have any configuration of slot depth, angle, orientation and shape to provide a desired range of articulated shapes, torque resistance and the like. The slots can have engaging features (not shown) to engage sleeve portions on either side of the slots 132 to increase torque resistance.

Referring to FIG. 3B, the distal end 135 of outer sleeve 126 and distal end 136 of inner sleeve 126 are coupled by connections to distal dielectric member 140 (described further below) to allow axial forces to be applied to inner sleeve 126 relative to outer sleeve 125 to thus articulate the articulating region 105 as is known in the art. The articulation mechanism is further described below. The notches or slots 132 in articulating regions 128 and 130 of sleeves 125 and 126, respectively, can have a width W that is uniform along the slotted region in the working end 102 or the slots can have a varying width. Alternatively, the slot width W can differ in different portions of the sleeve to effectuate a particular curved profile when fully articulated. In other variations, the slot width W can increase or decrease along the working end to create a curve having a varying radius. Clearly, it is understood that any number of variations are within the scope of this disclosure.

FIG. 4 is a sectional view of hub 118 of FIG. 1, wherein the proximal end 142 of outer sleeve 125 is fixed in the distal end 144 of hub 118. FIG. 4 further shows that the proximal end 146 of inner sleeve 126 is fixed in a threaded collar 148 that is adapted to move axially in order to translate the inner sleeve 126 relative to the outer sleeve 125. In FIG. 4, a drive coupling 155 is rotatable in a proximal end 156 of the hub 118. The drive coupling 155 has a slot configuration 158 that is adapted to mate with a shaft 160 (FIG. 2) of the motor drive unit 115 in handpiece 112. The interior of the drive coupling 155 has a threaded region 162 that engages the threaded region 164 of the threaded collar 148. Thus, it can be seen that the rotation of the drive coupling 155 will move the threaded collar 148 and inner sleeve 126 axially back and forth depending on the direction of rotation of the drive coupling 155 to articulate the working end 102 as shown in FIG. 1. In one variation, when the working end 102 is in a straight configuration, the drive coupling 155 can be rotated a selected amount from about 90° to 720°, or from about 90° to 360°, to thereby move the inner sleeve 126 in the proximal direction relative to the outer sleeve 125 to thus bend the working end 102 to an articulated configuration. As will be described further below, the articulation is driven by the motor drive 115 in the handpiece 102.

The electrosurgical functionality of the probe 100 can be described with reference to FIGS. 3A-3B and 4. In FIG. 3B, it can be seen that the inner and outer sleeves. 125 and 126, are connected at their distal ends. 135 and 136, to the distal dielectric member 140. The outer and inner sleeves 125, 126 are used as opposing polarity electrical leads that carry RF current to and from the active electrode 110 and a return electrode 170 which comprises an outer surface of outer sleeve 125. Therefore, the inner and outer sleeves (125, 126) must be spaced apart by an insulator, which at the distal end of the shaft 120 comprises the ceramic member 140. In FIG. 3B, it can be seen that the distal end 135 of outer sleeve 125 is mechanically locked to the ceramic member 140 by projecting portions 172a and 172b of the ceramic member 140 that are received by openings 174a and 174b in the wall of outer sleeve 125. The inner sleeve 126 has a distal end 136 with at least two projecting elements 165a and 165b that extend through first and second bores in the ceramic member 140 with the distal tips of the projecting elements 165a and 165b welded to active electrode 110.

Referring to FIG. 3A, the ceramic member 140 can be fabricated of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

In one variation, the ceramic member 140 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological. Mechanical and Optical Considerations", Chapter 17 in *Advances in Ceramics— Electric and Magnetic Ceramics. Bioceramics, Ceramics and Environment* (2011).

The ceramic member 140 can be fabricated of an yttria-stabilized zirconia as is known in the field of technical ceramics, and can be provided by CoorsTek Inc., 16000 Table Mountain Pkwy., Golden, Colo. 80403 or Superior Technical Ceramics Corp., 600 Industrial Park Rd., St. Albans City, Vt. 05478. Other technical ceramics that may be used consist of magnesia-stabilized zirconia, ceria-stabilized zirconia, zirconia toughened alumina and silicon nitride.

FIG. 3B further shows a thin wall insulator sleeve 175 in phantom view around the exterior of inner sleeve 126 to provide electrical insulation between the outer sleeve 125 and the inner sleeve 126. The insulator sleeve 175 can comprise a flexible temperature resistant material such as parylene. PFTE, PEEK or the like. The outer sleeve 125 can have a flexible thin-wall sheath 180 as shown in phantom view in FIG. 3A of a suitable polymer surrounding the articulating region 105 of the shaft assembly 120. In this variation, the return electrode 170 comprised a surface portion of outer sleeve 125 proximal from the articulating region 105 (FIG. 3A).

The components of hub 118 and cooperating handpiece that provide electrical pathways for delivering RF current to and from the probe working end 105 can now be described. As can be seen in FIGS. 1 and 4, the proximal hub 118 of probe 100 is configured with projecting elements 182 that cooperate with a J-lock grooves in the handpiece 102 (FIG. 2) for detachably locking the hub assembly 118 into the receiving passageway 185 of the handpiece 112.

In FIG. 4, it can be seen that a first spring-loaded electrical contacts 205A and 205B are disposed on opposing sides of hub 118 and are adapted to engage a corresponding metal electrical contact (not shown) in the receiving passageway 185 of handpiece 112. The probe hub 118 can be inserted into the receiving passageway 185 in handpiece 112 in either and "up" or "down" position, so the electrical contacts 205A and 205B are provided on both sides of the hub to provide contact with a corresponding electrical contact in the handpiece no matter the hub orientation. The spring-loaded electrical contacts 205A and 205B then extend inwardly in hub 118 to contact the rotating threaded coupling 148 that is a metal and is conductively fixed to proximal end 146 of inner sleeve 126. Thus, RF current can be carried through the threaded coupling 148 to the inner sleeve 126 and the active electrode 110 (FIG. 3B).

FIG. 4 shows a second spring-loaded electrical contact 210 in hub 118 that is configured to engage another electrical contact (not shown) in the receiving passageway 185 of handpiece 112 (FIG. 2). Electrical contact 210 extends inward in the hub 118 to contact the metal core 202 that is fixedly coupled to the proximal end 142 of outer sleeve 125, wherein a portion of the outer sleeve 126 is exposed and comprises the return electrode 170 as described above and illustrated in FIGS. 3A-3B. Inward of metal core 202 in the hub 118 is insulative plastic block 208 that has a bore 214 therein that allows for axial movement of the inner sleeve 126 to thereby articulate the working end 102.

Now turning to operation of the system. FIG. 2 shows that the handpiece 112 is operatively coupled by electrical cable 184 to a controller 185 and RF source 190. The controller 185 is adapted to control all operations of the motor drive 115 as well as RF functions. Actuator buttons 186a. 186b, 186c and a joystick 188 are provided on the handpiece 112 to actuate certain functions of the probe 100. In one variation, the joystick 188 is operatively coupled to the controller 185 to activate the motor drive 115 wherein pushing the joystick 188 forward activates the motor drive in a first rotational direction which in turn engages and rotates the drive coupling 155 in hub 118 to thereby articulate the working end 102 of the probe as shown in FIG. 1. In this variation, pushing on the joystick 188 can progressively move the working end between the linear configuration and the fully articulated configuration as indicated in FIG. 1. By releasing pressure on the joystick 188, the motor drive 115 would be de-activated and the working end 102 would remain articulated in any intermediate position between the linear configuration and fully articulated configuration of FIG. 1.

In another variation, the joystick 188 and a controller algorithm could operate so that a single push on the joystick 188 would articulate the working end 102 from the linear configuration to the fully articulated configuration of FIG. 1. Alternatively, a single touch of the joystick 188 could articulate the working end a predetermined number of degrees, wherein 2 to 10 touches of the joystick 188 would articulate the working end 102 from the linear configuration to the fully articulated configuration.

In another variation, the joystick 188 can be pressed backwards to activate rotation of the motor drive 115 in the opposite rotational direction to thereby articulate the working end 102 in the opposite direction compared to the articulation direction shown in FIG. 1.

Still referring to FIG. 2, one of the actuator buttons 186a. 186b or 186c on the handpiece 112 can be operatively coupled to the controller 185 and RF source 190 to energize the RF electrodes 110 and 170. In another variation, one of the actuator buttons, 186a, 186b or 186c is coupled to the controller 185 and the RF source 190 to select a particular mode or RF waveform, for example (1) an RF waveform for ablation or (2) an RF waveform for coagulation as is known in the art.

In another variation, referring to FIG. 2, the handpiece 112 has a display 195 (e.g., an LCD screen) that displays an image or other indicator of the articulated shape of the working end 102, as the motor drive articulates the working end. Such a display would be useful as the working end may not always be visible in an arthroscopic procedure, such as during insertion and withdrawal, and it would be important to provide the physician with an indication of the articulated shape of the working end 102.

In another variation, referring to FIGS. 2 and 3A-3B, the distal ceramic member 140 can have an aspiration port 230 therein that is connected to passageway 232 in the inner sleeve 126 that communicates through hub 118 and handpiece 112 with negative pressure source 220 (FIG. 2). In the embodiment shown in FIGS. 3A-3B, the aspiration port 230 extends through the electrode 110, but it should be appreciated that any number of ports can be provided in the working end in or near the active electrode 110.

In the embodiment of working end 102 shown in FIGS. 3A-3B, the active electrode 110 is disposed at the distal end of the ceramic member 140, but it should be appreciated that the active electrode 110 can have any suitable shape and configuration. For example, the active electrode can be on the side of the ceramic member 140 or can be configured as a ring electrode around the circumference of the ceramic member 140. Further, the active electrode can comprise a plurality spaced apart wire-like electrode elements that are known to be effective in rapidly forming and maintaining RF plasma for tissue ablation. In another variation, the active electrode can comprise a hook or blade electrode extends distally from the ceramic member 140. In still another variation, such a hook or blade electrode can be extendable and retractable from the ceramic member 140. In another variation, the electrode can be a motor-driven rotational cutting sleeve as is known in the art that can be coupled to negative pressure source 220 for cutting and extracting tissue. Such a cutting sleeve would have a flexible section to cooperate with the articulating section 105 of the working end 102.

Figure 5:
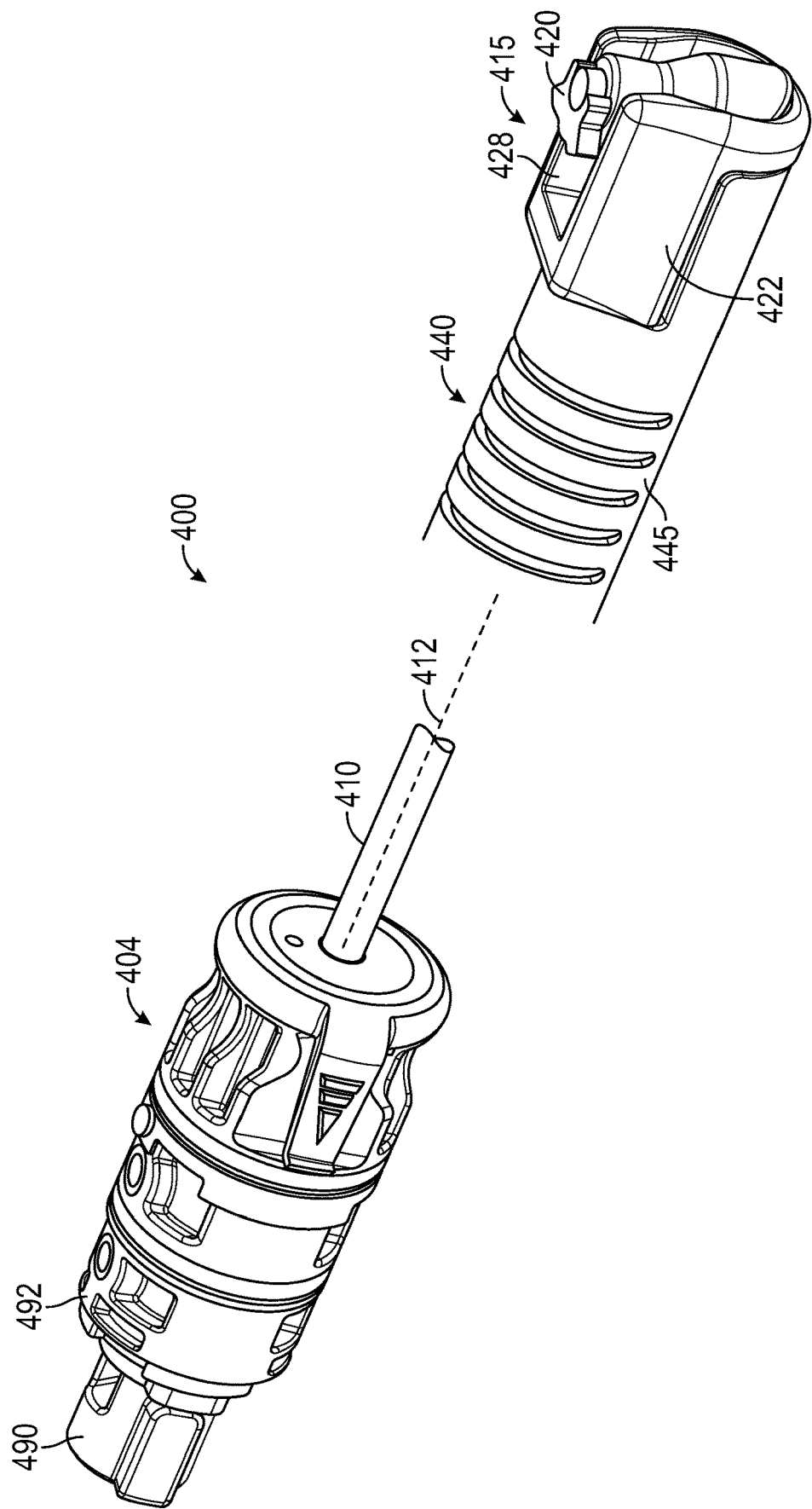
FIG. 5 is a perspective view of another variation of an articulating RF probe that has a motor driven reciprocating active electrode.
Figure 6:
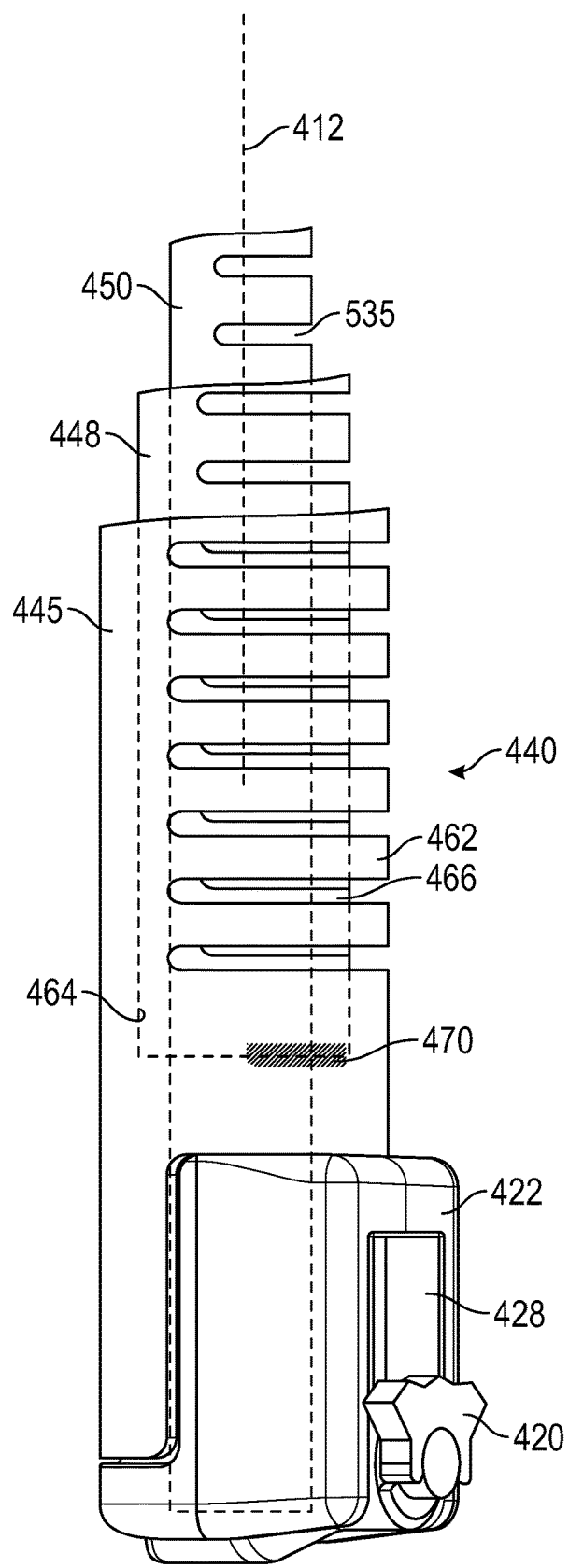
FIG. 6 is a cut-away view of the articulating region and working end of the articulating RF probe of FIG. 5.

Now turning to FIGS. 5-6, another variation of articulating probe 400 is shown that again has a hub 404 and elongate shaft 410 with longitudinal axis 412 that carries a distal electrosurgical working end 415. In this variation, an active electrode 420 is motor driven and is carried by the working end 415 and is adapted to reciprocate relative to a ceramic body or housing 422 wherein in the previous embodiment 100 of FIGS. 1 and 3A-3B, the active electrode 110 was fixed and stationary in the working end 102. In the variation of FIGS. 5-6, the working end 415 is of the type described in co-pending U.S. patent application Ser. No. 15/410,723 filed Jan. 19, 2017 titled ARTHROSCOPIC DEVICES AND METHODS in which the active electrode 420 reciprocates in a window 428 in the ceramic housing 422 carried at the distal end of the articulating region 440 of shaft 410. In the variation of FIG. 5, as in the previous embodiment, first and second concentric slotted sleeves. 445 and 448 respectively, are used to provide the articulating region 440 of the probe. In the variation of FIGS. 5-6, a third sleeve or member 450 is carried within an interior passageway 454 of the second sleeve 448 which is configured for reciprocation and extends through the shaft 410 and carries the active electrode 420. It should be appreciated that the third sleeve 450 in such an embodiment also can be configured for rotation or rotational oscillation or a combination of rotation and reciprocation.

The variation of FIG. 5 again is adapted for detachable coupling to the handpiece 112 and motor drive 115 of FIG. 2. The hub 404 of the probe 400 of FIG. 5 again has identical features as the previous embodiment of FIG. 1 including electrical contacts for coupling to the handpiece 112.

As can be understood from FIG. 2, the handpiece 112 and motor drive 115 essentially provide only two different operating outputs, which are first to rotate in clockwise direction and second to rotate in a counter-clockwise direction. In the previous embodiment of FIGS. 1-3, the motor drive 115 was adapted to rotate in a first direction to articulate the distal articulating region 105 (see FIGS. 1 and 3A) and then rotate in the opposite or second direction to de-articulate the articulating region 105 to return the shaft to a linear shape.

However, the probe of FIG. 5 requires three functions which are (i) to articulate the working end, (ii) to de-articulate the working end; and (iii) to reciprocate the active electrode 420.

Figure 7:
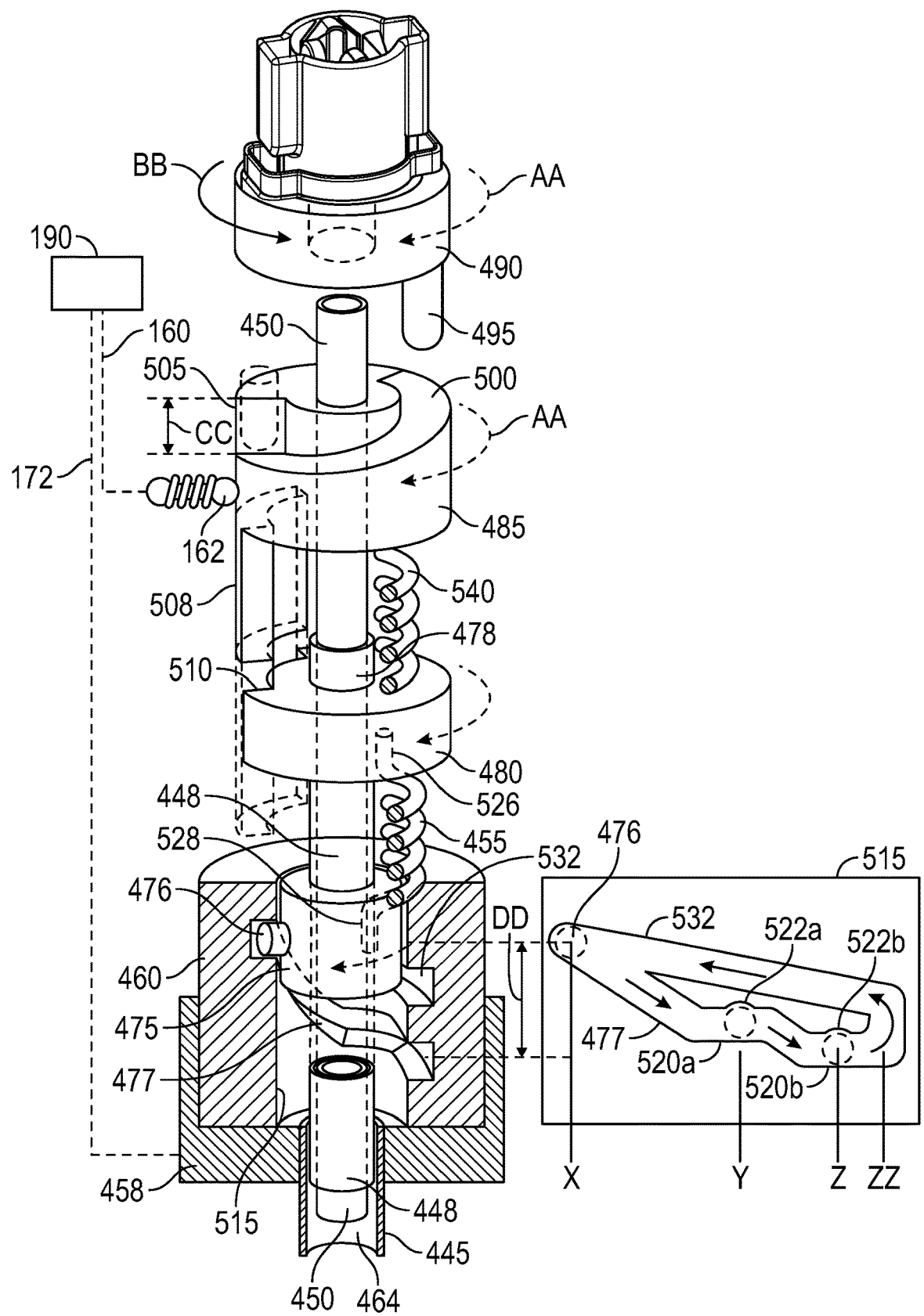
FIG. 7 is a schematic view of the mechanisms in the probe hub of FIG. 5 that allows the motor drive of FIG. 2 to both articulate and de-articulate the probe shaft of FIG. 5 and also reciprocate the active electrode.

FIG. 7 is a cut-away and exploded schematic view of the mechanisms in the interior of the hub 404 (FIG. 5) that provide the three functions listed above. The motor drive 115 of FIG. 2 when rotated in a first direction in cooperation with a distal compression spring 455 can articulate and de-articulate the working end. Then, the motor drive 115 can be rotated in the second or opposite rotational direction to reciprocate the active electrode 420 in the distal housing 422 as will be described in further detail below.

Referring to FIGS. 6-7, it can be understood that the shaft 410 and working end 415 that provide the articulating function comprise a first or outer sleeve 445 and the second concentric inner sleeve 448. The first sleeve 445 is fixed in distal hub body 458 that carries hub core 460. The first sleeve 445 has a slotted distal portion 462 as shown in FIGS. 5-6.

Referring to FIG. 7, the second sleeve 448 is adapted to move axially in the bore 464 of the first sleeve 445 and hub core 460. The second sleeve 448 also has a slotted distal portion 466 and a distal termination that is welded at weld 470 to the first or outer sleeve 445 (see FIG. 6) to provide articulation as described previously. The second sleeve 448 is fixed to a distal collar 475 that carries a transverse pin 476 that is adapted to move in an arcuate slot 477 in hub core 460 to thereby move the collar 475 axially relative to the first or outer sleeve 445. The proximal end 478 of the second sleeve 448 is also fixed to an intermediate collar 480 described further below. The third or innermost sleeve 450 which carries the active electrode 420 (FIG. 6) is fixed to a proximal collar 485 which is adapted to move back and forth axially relative to the first and second sleeves. 445 and 448, respectively.

Finally, FIG. 7 shows a drive coupling 490 in schematic view that is adapted to freely rotate without axial movement in a circumferential groove in a proximal end 492 of the hub 404 (see FIG. 5). The freely rotating drive coupling 490 in FIG. 7 is shown moved proximally away from the proximal collar 485.

Now describing the dual rotational mechanisms of FIG. 7 carried with the hub 404 in more detail, it can be seen that rotation of the drive coupling 490 in the first direction indicated by dashed arrows AA, will move the second sleeve 448 in the distal direction relative to the first sleeve 445 to thereby articulate the articulating region 440. In more detail, the controller and motor drive 115 can be configured to rotate the drive coupling 490 in the first direction at a slow speed and only a predetermined number of degrees. The controller 185 (FIG. 2) receives signals from Hall sensors that senses magnets in the drive coupling 490 to determine the rotational position of the drive coupling 490, as described in co-pending and commonly owned U.S. patent application Ser. No. 15/495,620 filed Apr. 24, 2017 titled ARTHROSCOPIC DEVICES AND METHODS. In this variation, the controller 185 again can initially determine the rotational position of the drive coupling 490 and then rotate the drive coupling as needed to any desired position.

Referring now to FIG. 6, it can be seen that the drive coupling 490 carries an extension member 495 that extends axially and which interfaces with the cam surface 500 of the proximal collar 485. As the drive coupling 490 rotates in the first direction, the extension member 495 moves along the cam surface 500 until it interfaces with the vertical surface 505. After the extension member 495 interfaces with the vertical surface 505, further rotation of the extension member 495 in the first direction then rotates the proximal collar 485. As can be seen in FIG. 7, the proximal collar 485 has an axially extending portion 508 that slidably engages a notch 510 in the intermediate collar 480. Further, the intermediate collar 480 is fixed to the second sleeve 448 and the assembly then when rotated also moves axially as the transverse pin 476 moves in the arcuate slot 477 in the hub core 460. From FIG. 7, it thus can be understood that rotation of the intermediate collar 480 causes the movement of transverse pin 476 in arcuate slot 477 to thereby push the second sleeve 448 axially in the distal direction which articulates the probe.

In the lower right portion of FIG. 7, the arcuate slot 477 in bore 515 of hub core 460 is shown in a flattened plane which illustrates the shape of slot 477 as the pin 476 moves within the surface of bore 515 in the hub core 460. It can be understood that rotation of distal collar 475 and transverse pin 476 can move along the arcuate slot 477 from an initial pin position X wherein the probe is not articulated to a second pin position Y wherein the probe is partly articulated to a third pin position Z wherein the probe is fully articulated. The arcuate slot 477 can have flat portions 520a and 520b with optional detents 522a and 522b where the pin 476 can rest to maintain the articulating region 440 in a particular articulated configuration. It should be appreciated that there may be several different flattened areas in the arcuate slot 477 to provide multiple degrees of articulation. As can be understood from FIG. 7, the distal compression spring 455 is adapted to urge the second sleeve 448 in the proximal direction relative to the first sleeve 445 to straighten the articulated working end and the flattened slot portions 520a and 520b prevent the spring from moving to pin along a slope in the slot 477. In FIG. 7, the maximum axial movement of the second sleeve 445 relative to stationary first sleeve 445 is indicated at extension distance DD which is the maximum axial movement of pin 476 pin slot 477.

As also can be seen in FIG. 7, the distal spring 455 can have a proximal end 526 fixed in the intermediate collar 480 and a distal end 528 fixed in the hub core 460 so the spring resists compression and also resists rotation. Thus, the distal spring 455 is adapted to urge the articulated region 440 of the probe (FIG. 5) toward a linear configuration. Again referring to the diagram of the lower right portion of FIG. 7, it can be understood that motor driven rotation of the collar 475 and pin 476 to position ZZ will then cause the pin 476 to move into the return portion 532 of arcuate slot 477 and thereafter return to the initial position X under the force of the distal spring 455.

Now turning to the reciprocation mechanism provided by the mechanisms shown in FIG. 7, it can be described how rotation of the drive collar 490 in the second direction indicated by the solid arrow BB will reciprocate the third sleeve 450 relative to the working end 415 in any articulated position to thereby reciprocate the active electrode 420 (see FIGS. 5-6). It should be appreciated that a distal portion 535 of the third sleeve 450 (FIG. 6) can be slotted in multiple orientations to thereby function as a flexible drive shaft within the passageway through the interior of the first and second sleeves, 445 and 448, when either straight or articulated.

In FIG. 7, it can be seen that rotation of the drive coupling 490 in the second direction (solid arrow BB) causes the extension pin 495 to ride along the cam surface 500 to thus move the proximal collar 485 distally until the extension pin 495 rotates over the vertical surface 505 which then allows the proximal collar 485 to move in the proximal direction under the force of proximal spring 540. Thus. FIG. 7 illustrates that the stroke of reciprocation indicated at CC is equivalent to the height of the vertical surface 505. The proximal spring 540 which resists compression is positioned between the proximal collar 485 and the intermediate collar 480 and urges the proximal collar in the proximal direction at all times.

Thus, it can be understood how the controller 185 by using the motor drive 115 can both articulate the working end of the probe 400 and reciprocate an active electrode 420 (FIG. 5) in the working end 415 during any degree of articulation of the working end.

Still referring to FIG. 7, the RF source 190 is shown schematically with a first electrical lead 160 coupled to a spring contact 162 that engages the proximal collar 485 which is a conductive metal and thus conducts RF current to the third sleeve 450 and the active electrode 420 at the working end. The second lead 172 from the RF source 190 extends to the distal hub 458 and is connected to the first sleeve 445 which comprises the return electrode as described previously. It should be appreciated each of the sleeves 445, 448 and 450 may have thin insulative coatings (not shown in FIG. 7) to thus insulate the RF current paths to the working end 415.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A disposable articulating probe attachable to a motorized handpiece, the disposable articulating probe comprising:
   an elongate shaft having a longitudinal axis and an articulating distal region, the elongate shaft comprising a first elongate sleeve and a second elongate sleeve, the second elongate sleeve longitudinally received in the first elongate sleeve, wherein a distal portion of the first elongate sleeve is fixed to a distal portion of the second elongate sleeve;
   a third elongate member longitudinally received in the second elongate sleeve such that at least part of the second elongate sleeve is positioned between the third elongate member and the first elongate sleeve along the elongate shaft,
   a hub for detachably connecting the disposable articulating probe to the motorized handpiece, the hub including a rotatable drive coupling at a proximal end of the hub for detachably engaging a rotating driver of the motorized handpiece when the disposable articulating probe is detachably connected to the motorized handpiece, wherein the rotatable drive coupling, when so detachably engaging the rotating driver, is rotatable about the longitudinal axis of the elongate shaft via rotation of the rotating driver,
   wherein the rotatable drive coupling is rotatable in a first direction about the longitudinal axis to cause a portion of the second elongate sleeve to move axially relative to a portion of the first elongate sleeve to articulate the articulating distal region of the elongate shaft,
   wherein the rotatable drive coupling is rotatable in a second direction about the longitudinal axis opposite the first direction to cause the third elongate member to axially reciprocate within the second elongate sleeve.

2. The disposable articulating probe of claim 1, wherein a proximal end of the first elongate sleeve is fixed in the hub.

3. The disposable articulating probe of claim 1 further comprising a distal ceramic member disposed at a distal end of the elongate shaft, wherein a distal portion of the third elongate member comprises an active electrode that axially reciprocates relative to the distal ceramic member when the rotatable drive coupling is rotated in the second direction about the longitudinal axis.

4. The disposable articulating probe of claim 1 further comprising a proximal collar that is fixed to a proximal portion of the third elongate member within the hub.

5. The disposable articulating probe of claim 4, wherein the rotatable drive coupling includes an extension member that extends distally within the hub to engage the proximal collar.

6. The disposable articulating probe of claim 5, wherein the proximal collar includes a sloped cam surface along which the extension member can slide when the rotatable drive coupling is rotated in the first direction or in the second direction about the longitudinal axis.

7. The disposable articulating probe of claim 6, wherein the proximal collar includes a vertical surface adjacent the sloped cam surface.

8. The disposable articulating probe of claim 7, wherein the rotatable drive coupling is rotatable in the first direction about the longitudinal axis to cause the extension member to slide along the sloped cam surface in the first direction until the extension member contacts the vertical surface which prevents the extension member from sliding any further along the sloped cam surface in the first direction.

9. The disposable articulating probe of claim 8 further comprising a distal collar that is fixed to a proximal portion of the second elongate sleeve within the hub.

10. The disposable articulating probe of claim 9, wherein the rotatable drive coupling is rotatable in the first direction about the longitudinal axis while the extension member is contacting the vertical surface to cause the distal collar to rotate in the first direction about the longitudinal axis.

11. The disposable articulating probe of claim 10, wherein the distal collar includes a transverse pin that can travel within an arcuate slot in the hub when the distal collar rotates in the first direction or in the second direction about the longitudinal axis.

12. The disposable articulating probe of claim 11, wherein the transverse pin is positionable in a first pin position in the arcuate slot that corresponds to a non-articulated condition of the articulating distal region of the elongate shaft, and wherein the distal collar is rotatable in the first direction about the longitudinal axis to move the transverse pin from the first pin position to a second pin position to cause the second elongated sleeve to move distally relative to the first elongated sleeve to move the articulating distal region of the elongate shaft from a non-articulated condition to a first articulated condition.

13. The disposable articulating probe of claim 12, wherein, while the articulating distal region of the elongate shaft is maintained in the first articulated condition, the rotatable drive coupling is rotatable in the second direction about the longitudinal axis to axially reciprocate the third elongate member within the second elongate sleeve.

14. The disposable articulating probe of claim 12 further comprising a distal compression spring that extends proximally from the distal collar within the hub, wherein, when the transverse pin is positioned away from the first pin position in the arcuate slot, the distal compression spring is effective to urge movement of the transverse pin back to the first pin position to thereby move the second elongated sleeve proximally relative to the first elongated sleeve to thereby return the articulating distal region of the elongate shaft back to the non-articulated condition.

15. The disposable articulating probe of claim 14, wherein the arcuate slot includes a flat portion with a detent in which the transverse pin can rest when the transverse pin is in the second pin position.

16. The disposable articulating probe of claim 14, wherein the distal collar is rotatable in the first direction about the longitudinal axis to move the transverse pin from the second pin position back to the first pin position along a return portion of the arcuate slot and thereby return the articulating distal region of the elongate shaft back to the non-articulated condition.

17. The disposable articulating probe of claim 6, wherein the rotatable drive coupling is rotatable in the second direction about the longitudinal axis to cause the extension member to slide along the sloped cam surface in the second direction to move the proximal collar and the third elongate member distally relative to the second elongate sleeve.

18. The disposable articulating probe of claim 17, wherein the proximal collar includes a vertical surface adjacent the sloped cam surface.

19. The disposable articulating probe of claim 18, wherein the extension member is rotatable in the second direction about the longitudinal axis until rotating over the vertical surface, the vertical surface corresponding to a stroke of reciprocation of the third elongate member relive to the second elongated sleeve.

20. The disposable articulating probe of claim 18 further comprising a proximal compression spring that extends distally from the proximal collar within the hub, the proximal compression spring effective to urge movement of the proximal collar proximally relative to the second elongate sleeve when the extension member rotates past the vertical surface when rotating in the second direction about the longitudinal axis.

21. The disposable articulating probe of claim 1, wherein the rotatable drive coupling is rotatable in the first direction about the longitudinal axis to cause a pin that extends transversely from the second elongate sleeve to move within an arcuate slot in the hub in the first direction to cause the portion of the second elongate sleeve to move axially relative to the portion of the first elongate sleeve to articulate the articulating distal region of the elongate shaft.

22. The disposable articulating probe of claim 21, wherein the arcuate slot provides a continuous path along which the pin can travel in the first direction for converting the articulating distal region of the elongate shaft from a non-articulated condition to an articulated condition and back to the non-articulated condition.

\* \* \* \* \*

UNITED STATES PATENT AND TRADEMARK OFFICE
CERTIFICATE OF CORRECTION

| | | |
|---|---|---|
| PATENT NO. | : 11,766,291 B2 | |
| APPLICATION NO. | : 17/143739 | |
| DATED | : September 26, 2023 | |
| INVENTOR(S) | : Germain et al. | |

It is certified that error appears in the above-identified patent and that said Letters Patent is hereby corrected as shown below:

In the Claims

In Column 14, Line 30, in Claim 12, delete "a non-articulated" and insert --the non-articulated-- therefor In Column 15, Line 5, in Claim 19, delete "relive" and insert --relative-- therefor Signed and Sealed this
Twenty-first Day of November, 2023

Katherine Kelly Vidal
*Director of the United States Patent and Trademark Office*